United States Patent [19]
Pelosi, Jr. et al.

[11] Patent Number: 5,994,354
[45] Date of Patent: Nov. 30, 1999

[54] CYCLIC URETHANES USEFUL AS ANTIARRHYTHMIC AND ANTIFIBRILLATORY AGENTS

[75] Inventors: Stanford Salvatore Pelosi, Jr.; Chia-Nien Yu, both of Norwich, N.Y.

[73] Assignee: The Procter & Gamble Company, Cincinnati, Ohio

[21] Appl. No.: 08/479,254

[22] Filed: Jun. 7, 1995

Related U.S. Application Data

[63] Continuation of application No. 08/352,270, Dec. 7, 1994, abandoned, which is a continuation of application No. 08/087,150, Jul. 2, 1993, abandoned, which is a continuation of application No. 07/744,865, Aug. 14, 1991, abandoned.

[51] Int. Cl.$^6$ .................... A61K 31/445; A61K 31/495; C07D 413/14
[52] U.S. Cl. .................... 514/252; 514/326; 544/369; 546/209
[58] Field of Search .................... 514/252, 376, 514/326; 546/209; 548/230; 544/369

[56] References Cited

U.S. PATENT DOCUMENTS

| | | | |
|---|---|---|---|
| 2,802,002 | 8/1957 | Gever et al. | 548/230 |
| 3,318,878 | 5/1967 | Dunn | 546/209 |
| 3,415,821 | 12/1968 | Davis et al. | 548/318.1 |
| 3,598,812 | 8/1971 | Hoyle et al. | 548/230 |
| 3,839,567 | 10/1974 | Rufer et al. | 514/376 |
| 3,906,101 | 9/1975 | Hoyle et al. | 514/376 |
| 4,393,204 | 7/1983 | Pelosi, Jr. | 548/230 |
| 4,543,359 | 9/1985 | Ellis et al. | 514/390 |
| 4,689,341 | 8/1987 | Diamond et al. | 514/399 |
| 4,705,799 | 11/1987 | Gregory | 548/229 |
| 4,707,499 | 11/1987 | Baran et al. | 514/471 |
| 4,713,832 | 12/1987 | Pascal | 544/255 |
| 4,720,580 | 1/1988 | Buzby et al. | 564/89 |
| 4,775,670 | 10/1988 | Sykes et al. | 514/210 |
| 4,870,095 | 9/1989 | Bailey | 548/374 |
| 4,876,262 | 10/1989 | Oinuma et al. | 546/209 |
| 4,882,354 | 11/1989 | Huang et al. | 514/461 |
| 4,886,794 | 12/1989 | Walsh | 546/209 |
| 4,895,867 | 1/1990 | Huang et al. | 514/397 |
| 4,963,561 | 10/1990 | Lesher et al. | 546/118 |
| 4,966,967 | 10/1990 | Lumma, Jr. et al. | 540/568 |
| 5,066,662 | 11/1991 | Hobbs et al. | 514/252 |
| 5,086,055 | 2/1992 | Walsh et al. | 544/369 |
| 5,091,426 | 2/1992 | Pelosi | 514/252 |

FOREIGN PATENT DOCUMENTS

| | | |
|---|---|---|
| 0235752 | 9/1987 | European Pat. Off. . |
| 0347733 | 12/1989 | European Pat. Off. . |
| 0431945 | 12/1991 | European Pat. Off. . |
| 47-49588 | 12/1972 | Japan ........... 548/230 |
| 398599 | 3/1966 | Switzerland ........... 548/230 |
| 93-04064 | 3/1993 | WIPO . |

OTHER PUBLICATIONS

Bigger, J. T. and Hoffman, B. F., "Antiarrhythmic Drugs", Ch. 35 in Goodman and Gilman's The Basis of Pharmaceutical Therapeutics, 8th ed., ed., A. G. Gilman, pp. 840–873 (1990).

Bigger, J. T., "Antiarrhythmic Treatment: An Overview", American Journal of Cardiology, vol. 53, pp. 8B–16B, Feb. 27, 1984.

Woosley, R. L., "Antiarrhythmic Agents", in The Heart, Ch. 95, pp. 1682–1711, ed. J. W. Hurst, New York, McGraw–Hill (1990).

Woosley, R. L., "Antiarrhythmic Drugs", Annual Review. Pharmacology and Toxicology, vol. 31, pp. 427–455 (1991).

Morganroth, J. and Bigger, J. T., "Pharmacological Management of Ventricular Arrhythmias After the Cardiac Arrhythmia Suppression Trial", American Journal of Cardiology, vol. 65, pp. 1497–1503 (1990).

Goldstein, S., "Toward a New Understanding of the Mechanism and Prevention of Sudden Death in Coronary Heart Disease", Circulation, vol. 82(1): pp. 284–288 (1990).

Echt, D. S. et al. Mortality and Morbidity in Patients Receiving Encainide, Flecainide, or Placebo: The Cardiac Arrhythmia Suppression Trial, New England Journal of Medicine, vol. 324, pp. 781–788 (1991).

(List continued on next page.)

Primary Examiner—Richard L. Raymond
Attorney, Agent, or Firm—James C. Kellerman; Carl J. Roof; Karen F. Clark

[57] ABSTRACT

The novel cyclic urethanes, and their pharmaceutically-acceptable salts and esters, described herein which are useful as antiarrhythmic and antifibrillatory agents and have the following general structure:

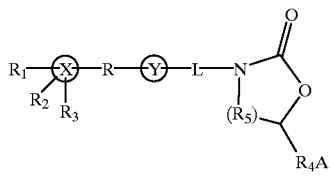

wherein (a) X is a saturated or unsaturated, 5-, 6-, or 7-membered heterocycle or carbocycle;

(b) Y is a substituted or unsubstituted, saturated or unsaturated, 5-, 6-, or 7-membered heterocyclic ring or carbocyclic ring, or is nil;

(c) L is selected from the group consisting of alkylamino, alkenylamino, alkylimino, alkenylimino and acylamino; wherein the nitrogen atom thereof is bound to the nitrogen atom at the 3-position of the cyclic urethane ring moiety;

(d) A is a substituted or unsubstituted, saturated or unsaturated, straight-chain or branched, $C_1$–$C_8$ heteroalkyl; or a substituted or unsubstituted, saturated or unsaturated heterocycle having 6- or 7-members which may not have an oxygen atom; and A has one nitrogen atom which is adjacent to $R_4$; and and the pharmaceutically-acceptable salts and esters thereof.

16 Claims, No Drawings

OTHER PUBLICATIONS

Coplen, S. E. et al. "Efficacy and Safety of Quinidine Therapy for Maintenance of Sinus Rhythm After Cardioversion: A Meta-analysis" Circulation, vol. 82, pp. 1106–1116 (1990).

Swirska, A. et al., "Derivatives of 5–Piperidinomethyl–3–amino–2–oxazolidone with Expected Hypotensive Action", *Acta Polon. Pharm.* 23 (No. 2):93–96, 1996.

Swirska et al. Chem. Abstr. vol. 65 Entry 10575a (1966.

CYCLIC URETHANES USEFUL AS ANTIARRHYTHMIC AND ANTIFIBRILLATORY AGENTS

This is a continuation of case Ser. No. 08/352,270, filed Dec. 7, 1994, now abandoned, which is a continuation of case Ser. No. 08/087,150 filed Jul. 2, 1993, now abandoned, which is a continuation of case Ser. No. 07/744,865, filed Aug. 14, 1991, now abandoned.

BACKGROUND OF THE INVENTION

The present invention relates to cyclic urethane compounds, and pharmaceutical compositions thereof, useful in treating humans or other mammals with cardiac arrhythmia and/or cardiac fibrillation.

The cyclic urethane compounds disclosed herein are active as antifibrillatory and antiarrhythmic agents. The present compounds exhibit broad efficacy against cardiac arrhythmia and fibrillation and can be satisfactorily applied to substantially alleviate and/or prevent arrhythmia and fibrillation. In addition, said compounds exhibit a lower incidence of some of the undesirable side effects than do many of the conventional antiarrhythmic therapies. An additional benefit of the compounds described herein is that they exhibit both antifibrillatory and antiarrhythmic activity; conventional therapies generally do not exhibit efficacy as antifibrillatory agents. See e.g. Coplen, S. E. et al., "Efficacy and Safety of Quinidine Therapy for Maintenance of Sinus Rhythm after Cardioversion—A meta-analysis, *Circulation*, Vol. 82, pp. 1106–1116,(1990); and Echt, D. S. et al., "Mortality and Morbidity in Patients receiving Ecainide, Flecainide, or Placebo: The Cardiac Arrhythmia Suppression Trial", *N. Enql. J. Med.*, Vol. 324, pp. 781–788 (1991), both hereby incorporated by reference herein.

In a healthy, structurally-sound heart, the precise, sequential electrical activation, then deactivation, of the entire cardiac muscle that occurs unerringly with each beat is characterized as normal cardiac rhythm. Arrhythmias are characterized as occurrences of abnormal electrical activity that can interfere with normal cardiac rhythm. The abnormal electrical activity can interfere with the initiation of, and/or the uniform spread of, the electrical wave (i.e. depolarization followed by repolarization of the cardiac muscle) that triggers the heart to contract. The disruption of the smooth, cyclical process of cardiac function associated with normal cardiac rhythm by the existence of arrhythmias is, in some instances, life-threatening.

Arrhythmias range in severity from relatively benign (consisting of asymptomatic and infrequent premature ventricular complexes [PVCs]) to life-threatening (consisting of ventricular fibrillation, and sustained ventricular tachyarrhythmia). For an excellent review of arrhythmias and an overview of antiarrhythmic therapy, see, e.g. Bigger, Thomas J., "Antiarrhythmic Treatment: An Overview", *American Journal of Cardiology*, Vol. 53, pp. 8B–16B, Feb. 27, 1984; Goldstein, S. "Toward a New Understanding of the Mechanism and Prevention of Sudden Death in Coronary Heart Disease, *Circulation*, Vol. 82 (1), pp. 284–88 (1990); and Woosley, R. L., "Antiarrhythmic Drugs" *Annu. Rev. Pharmacal. Toxical.* Vol. 31: pp. 427–455, (1991), all hereby incorporated by reference herein. Life-threatening arrhythmias are noted as a leading cause of death worldwide. For instance, it is estimated that sudden cardiac death resulting from ventricular fibrillation kills approximately 400,000–600,000 people in the United States each year. U.S. Department of Health and Human Services (1985) NCHS Monthly Vital Statistics Report 33:8–9.

Arrhythmias are generally classified into two types: 1) Supraventricular Arrhythmias (for example, atrial fibrillation and flutter) and 2) Ventricular Arrhythmias (for example, ventricular tachyarrhythmia and ventricular fibrillation and flutter).

Supraventricular arrhythmias are generally not life-threatening. Individuals with these arrhythmias may experience a wide range of symptoms, from slight to severe intensity. These individuals may feel the physical sensation of missed beats, extra beats, and/or flutter, may occasionally feel slightly light-headed or dizzy, and may have shortness of breath and/or chest pain. Since this situation is, in fact, generally not life threatening, more aggressive therapies such as conventional antiarrhythmic drugs are sometimes not prescribed, because the side effects usually associated therewith may not be acceptable for a non-life-threatening condition. However, the the cyclic urethane compounds described herein are generally much better tolerated than many of the conventional, currently available antiarrhythmics; therefore, they would be an acceptable therapy for many patients suffering from supraventricular arrhythmias and would substantially alleviate the discomfort these individuals experience.

Ventricular arrhythmias, on the other hand, are potentially much more serious and have been classified into three groups: 1) benign; 2) prognostically-significant (potentially lethal);

and 3) life threatening (lethal). See, e.g. Morganroth, J. and Bigger, J. T., "Pharmacological Management of Ventricular Arrhythmias after the Cardiac Arrhythmia Suppression Trial," *Amer. J. Cardiol.* Vol. 65, pp. 1497–1503, 1990, (hereinafter *Morganroth & Bigger*), hereby incorporated by reference herein.

Individuals with benign arrhythmias exhibit very low risk of sudden death, cardiac scarring, and heart disease. Benign ventricular arrhythmias are relatively common and account for approximately 30% of all ventricular arrhythmias. Id. Benign arrhythmias, such as premature ventricular complexes (PVCs), pose minimal risks to individuals and rarely require antiarrhythmic therapy. However, the PVCs may be of a frequency or complexity, or are associated with sufficiently alarming symptoms, so that individuals experiencing them do not respond to reassurance that the arrhythmias and symptoms are not dangerous. They also may not respond to more conventional treatment (e.g. beta-blockers). In these cases, treatment with the compounds described herein will likely be beneficial to these individuals.

Prognostically-significant arrhythmias are associated with some additional clinical presentation of cardiac disease, such as mild heart failure, ischemic symptoms, and/or cardiac scarring. It has been stated that approximately 65% of all ventricular arrhythmias are prognostically significant. See, e.g. *Morganroth & Bigger*, at 1497.

Patients with life-threatening arrhythmias may present with syncope (sudden loss of consciousness—usually fainting—associated with insufficient brain perfusion), cardiac arrest, heart failure, and/or myocardial ischemia, in the presence of structural heart disease. Life-threatening arrhythmias are relatively uncommon; probably less than 10% of the individuals suffering from arrhythmias suffer from a lethal form. See *Morganroth & Bigger* at 1497. However, due to the life-threatening nature of lethal ventricular arrhythmias and the severity of symptoms, they must be aggressively treated.

The cyclic urethane compounds described herein are efficacious against cardiac fibrillation and supraventricular and ventricular arrhythmias. In addition, the said compounds exhibit less of the side effects which have come to be tolerated in traditional antiarrhythmic therapy, for lack of acceptable alternate therapies. For example, many current therapies cause pulmonary toxicity, cardiac depression, and neurologic effects not specific to cardiac tissue. For an excellent discussion of the side effects associated with conventional antiarrhythmic therapies see, Bigger, J. T. and Hoffman, B. F., "Antiarrhythmic Drugs" in *Goodman and Gilman's The Basis of Pharmacological Therapeutics*, 8th edition, ed. A. G. Gilman, pp. 840–873, New York: Pergamon; and Woolsey, R. L. "Antiarrhythmic Agents", in *The Heart*, ed. J. W. Hurst, pp. 1682–1711. New York: McGraw-Hill (1990), both incorporated by reference herein.

In addition, the compounds described herein are readily bioavailable, which facilitates treatment by oral administration, and therefore greatly facilitates patient compliance. In addition, the compounds described herein are relatively inexpensive to manufacture, and they exhibit a high degree of stability in oral dosage forms.

SUMMARY OF THE INVENTION

The novel cyclic urethanes described herein, and their pharmaceutically-accepted salts and esters, which are useful as antiarrhythmic and antifibrillatory agents have the following general structure:

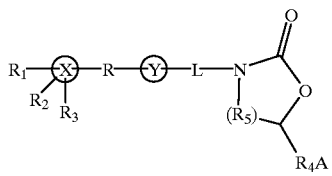

wherein (a) X is a saturated or unsaturated, 5-, 6-, or 7-membered heterocycle or carbocycle;

(b) R is selected from the group consisting of covalent bond, nil, heteroatom, carbonyl, heterocyclic ring, carbocyclic ring, alkyl, alkenyl, alkoxy, alkylamino, arylalkyl, aryloxy, acyl, acyloxy, and acylamino;

(c) Y is a substituted or unsubstituted, saturated or unsaturated, 5-, 6-, or 7-membered heterocyclic ring or carbocyclic ring, or is nil;

and wherein when R is nil, X and Y are fused ring systems; and when R is a covalent bond, X and Y are ring systems linked through a covalent bond; and when Y is nil, R is a covalent bond, and X is a carbocycle bound to L through R;

(d) $R_1$, $R_2$, and $R_3$ are independently selected from the group consisting of nil, Cl, F, Br, $NH_2$, $CF_3$, OH, $SO_3H$, $CH_3SO_2NH$, COOH, alkoxy, alkyl, alkoxycarbonyl, hydroxyalkyl, carboxyalkyl, aminoalkyl, acylamino, and acyloxy;

(e) L is selected from the group consisting of alkylamino, alkenylamino, alkylimino, alkenylimino and acylamino; wherein the nitrogen atom thereof is bound to the nitrogen atom at the 3-position of the cyclic urethane ring moiety;

(f) $R_4$ is selected from the group consisting of alkyl, alkenyl, alkynyl, alkylacyl, and heteroalkyl;

(g) A is a substituted or unsubstituted, saturated or unsaturated, straight-chain or branched, $C_1$–$C_8$ heteroalkyl; or a substituted or unsubstituted, saturated or unsaturated heterocycle having 6- or 7-members which may not have an oxygen atom; and A has one nitrogen atom which is adjacent to $R_4$; and (h) $R_5$ is a substituted or unsubstituted $C_1$ or $C_2$ alkyl;

The Ring System (X-R-Y)

The cyclic urethane compounds described herein are comprised of a cyclic urethane moiety connected to a ring system (X-R-Y) via a linking moiety (L). The cyclic urethanes have a nitrogen atom at the 3-position, and are substituted at the 5-position (when the cyclic urethane moiety is a 5-membered ring) or at the 6-position (when the cyclic urethane moiety is a 6-membered ring) with an amino-containing moiety (A). A is separated from the carbon atom to which it is bound by a spacing group ($R_4$). The moiety represented by (X-R-Y) is a ring system moiety and consists of one carbocyclic ring or two or more fused or unfused, saturated or unsaturated, substituted or unsubstituted, carbocyclic rings or heterocyclic rings as defined herein. When there is only one ring in the X-R-Y moiety, the ring is a carbocycle. When there are two or more rings, the rings may be carbocycles and/or heterocycles and each ring may contain 5, 6, or 7, preferably 5 or 6, members.

It is preferable that the ring system (X-R-Y) is polycyclic and is comprised of two, unfused rings and even more preferable that the ring represented by Y which is adjacent to the linking moiety, L, be a heterocycle, most preferably a five-membered ring which contains an oxygen heteroatom at the 1-position. In addition, when there are two rings in the ring system, it is also preferable that the heterocycle (Y) is covalently bound to the other ring (X) at the 5-position of the heterocycle Y and at the 1-position of the ring X, and that the heterocycle Y is bound to the L moiety at the 2-position of the heterocycle Y.

Although not preferred, it is also possible for the polycyclic ring system (X-R-Y) to consist of two rings (X and Y) which are separated by an alkyl, carbonyl, or a heteroatom, most preferably oxygen (R). In addition, the ring system may be monocyclic, and consist of one carbocyclic ring; in this case, Y is nil and R is a covalent bond attached to L. However, when there is only one carbocyclic ring in the system, the ring is preferably substituted with at least two, and most preferably at least three, substituents chosen from the group consisting of, but not limited to, hydroxy, methyl, Cl, methoxy, and benzoyl.

When substituted, any or all of the members of the ring system (whether monocyclic or polycyclic) may have one or more substituents, and may be substituted with Cl, F, Br, $NH_2$, $CF_3$, OH, $SO_3H$, $CH_3SO_2NH$, COOH, alkoxy, alkyl, alkoxycarbonyl, hydroxyalkyl, carboxyalkyl, aminoalkyl, acylamino or acyloxy.

The Linking Moiety (L)

L is the linking moiety of the novel cyclic urethane compounds of the present invention. The carbon-containing end of L is bound on to the ring system, at Y, but if Y is nil, at X; most preferably at the 2-position of the Y ring or at the 1-position of the X ring, if Y is nil. The nitrogen atom of the L moiety is bound to the nitrogen atom at the 3-position of the cyclic urethane moiety. The L moiety is selected from the group consisting of, but not limited to, alkylamino, alkenylamino, alkylimino, alkenylimino, and acylamino; L is preferably an alkylimino, most preferably a $C_1$ alkylimino, CH=N.

The Cyclic Urethane Moiety

The cyclic urethane moiety of the novel compounds of the present invention gives the novel compounds of the present invention their characteristic name. The cyclic urethane moiety may be a 5- or 6-membered ring, preferably a 5-membered ring. The cyclic urethane moiety is connected to the nitrogen atom of the linking moiety (L) at the nitrogen atom at the 3-position of the cyclic urethane moiety. The cyclic urethane moiety of the novel compounds of the present invention has the following structure:

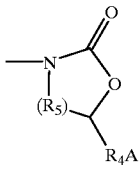

wherein $R_5$ is a $C_1$ or $C_2$ alkyl, preferably a $C_1$ alkyl. A must have one nitrogen atom adjacent to $R_4$ and A is either a heteroalkyl or a 6- or 7-membered heterocyclic ring wherein the heteroatoms are nitrogen or sulfur, and may not contain an oxygen atom. When A is a heteroalkyl, A may be straight-chained or branched, saturated or unsaturated, substituted or unsubstituted. When A is a heterocycle, A is a 6- or 7-membered heterocyclic ring, which may not have an oxygen atom and may contain one or two heteroatoms, nitrogen or sulfur, one of which must be a nitrogen atom attached to $R_4$. Said ring may be substituted or unsubstituted, preferably substituted, and saturated or unsaturated, preferably saturated. $R_4$ is a substituent at the 5-position (when the cyclic urethane moiety is a 5-membered ring) or at the 6-position (when the cyclic urethane moiety is a 6-membered ring) of the cyclic urethane moiety and is connected to a nitrogen atom of A. $R_4$ is selected from the group consisting of, but not limited to alkyl, alkenyl, alkynyl, alkylacyl, and heteroalkyl.

When A is a substituted heteroalkyl, the substituents are selected from the group consisting of, but not limited to, methyl, hydroxyethyl, alkyl, aryl, heterocycle, arylalkyl, mercaptoethyl, and methanesulfonyl.

When heterocycle A has two heteroatoms and both are nitrogen, it is preferable that the nitrogen atom not adjacent to $R_4$ be substituted with substituents selected from the group consisting of, but not limited to, methyl, hydroxyethyl, alkyl, aryl, heterocycle, arylakyl, mercaptoethyl, and methanesulfonyl. When heterocycle A has only 1 nitrogen atom, it is preferable that the heterocycle be substituted (at the position para to the nitrogen connected to $R_4$ if the heterocycle has 6-members) with substituents selected from the group consisting of, but not limited to, hydroxyethyl, hydroxy, oxo, and methyl.

In addition to the novel cyclic urethane compounds described herein, the invention described herein also relates to novel pharmaceutical compositions containing the novel cyclic urethane compounds of the present invention, and to a method of treatment for cardiac arrhythmia and fibrillation utilizing the various amino-substituted cyclic urethane compounds as described herein.

Definitions and Usage of Terms

The following is a list of definitions for terms used herein.

"Heteroatom" is a nitrogen, sulfur, or oxygen atom. Groups containing one or more heteroatoms may contain different heteroatoms.

"Alkyl" is an unsubstituted or substituted, straight-chain or branched, saturated hydrocarbon chain having 1 to 8 carbon atoms, and preferably, unless otherwise stated, from 1 to 4 carbon atoms. Preferred alkyl groups include, but are not limited to, methyl, ethyl, propyl, isopropyl, and butyl.

"Heteroalkyl" as used herein is an unsubstituted or substituted, saturated chain having from 3 to 8-members and comprising carbon atoms and one or two heteroatoms.

"Alkenyl" is an unsubstituted or substituted, straight-chain or branched, hydrocarbon chain having from 2 to 8 carbon atoms, preferably from 2 to 4 carbon atoms, and having at least one olefinic double bond.

"Alkynyl" is an unsubstituted or substituted, straight-chain or branched, hydrocarbon chain having from 2 to 8 carbon atoms, preferably from 2 to 4 carbon atoms, and having at least one triple bond.

"Ring System" as used herein refers to the ring-containing moiety to which the cyclic urethane moiety is connected through the linking moiety, L. It is denoted herein by "X-R-Y" and may be a monocyclic ring moiety, or a fused, bridged, or spiro polycyclic ring moiety, and may contain carbocycles, heterocycles, or both. Monocyclic rings generally contain from 3 to 8 atoms, preferably 5 to 7 atoms. Polycyclic ring systems consisting of two rings generally contain 6 to 16, preferably from 10 to 12 atoms. Polycyclic ring systems consisting of three rings generally contain 13 to 17 atoms, preferably 14 to 15 atoms.

"Carbocyclic ring" or "Carbocycle" as used herein is an unsubstituted or substituted, saturated, unsaturated or aromatic, hydrocarbon ring, generally containing from 3 to 8 atoms, preferably 5 to 7 atoms.

"Heterocyclic ring" or "Heterocycle" as used herein is an unsubstituted or substituted, saturated or unsaturated or aromatic ring comprised of carbon atoms and one or more heteroatoms in the ring. Heterocyclic rings generally contain from 3 to 8, preferably 5 to 7, atoms. Unless otherwise stated, the heteroatom may be independently chosen from nitrogen, sulfur, and oxygen.

"Aryl" is an aromatic carbocyclic ring. Preferred aryl groups include, but are not limited to, phenyl, tolyl, xylyl, cumenyl, and naphthyl.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g. —O-alkyl or —O-alkenyl). Preferred alkoxy groups include, but are not limited to, methoxy, ethoxy, propoxy, and alkyloxy.

"Hydroxylalkyl" is a substituted hydrocarbon chain which has a hydroxy substituent (e.g. —OH), and may have other substituents. Preferred hydroxyalkyl groups include, but are not limited to, hydroxyethyl, hydroxypropyl, phenylhydroxalkyl.

"Carboxyalkyl" is a substituted hydrocarbon chain which has a carboxy substituent (e.g. —COOH) and may have other substituents. Preferred carboxyalkyl groups include carboxymethyl, carboxyethyl, and their acids and esters.

"Aminoalkyl" is a hydrocarbon chain, (e.g. alkyl) substituted with an amine moiety (e.g. NH-alkyl-), such as dimethylamino alkyl.

"Alkylamino" is an amino moiety having one or two alkyl substituents (e.g. —N-alkyl).

"Alkenylamino" is an amino moiety having one or two alkenyl substituents (e.g. —N-alkenyl).

"Alkynylamino" is an amino moiety having one or two alkynyl substituents (e.g. —N-alkynyl).

"Alkylimino" is an imino moiety having one or two alkyl substituents (e.g. N=alkyl-).

"Arylalkyl" is an alkyl moiety substituted with an aryl group. Preferred arylalkyl groups include benzyl and phenylethyl.

"Arylamino" is an amino moiety substituted with an aryl group (e.g. —NH-aryl).

"Aryloxy" is an oxygen atom having an aryl substituent (e.g. —O-aryl).

"Acyl" or "carbonyl" is a moiety formed by removal of the hydroxy from a carboxylic acid (e.g. R—C(=O)—). Preferred alkylacyl groups include, but are not limited to, acetyl, propionyl, and butanoyl.

"Acyloxy" is an oxygen atom having an acyl substituent (e.g. —O-acyl); for example, —O—C(=O)-alkyl.

"Acylamino" is an amino moiety having an acyl substituent (e.g. —N-acyl); for example, —NH—(C=O)-alkyl.

"Halo", or "halogen", or "halide" is a chloro, bromo, fluoro, or iodo atom radical. Chloro, bromo, and fluoro are preferred halides.

Also, as referred to herein, a "lower" hydrocarbon moiety (e.g., "lower" alkyl) is a hydrocarbon chain comprised of from, unless otherwise stated, 1 to 6, preferably from 1 to 4, carbon atoms.

A "pharmaceutically-acceptable" salt is a catonic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred catonic salts include the alkali-metal salts (such as sodium and potassium), and alkaline earth metal salts (such as magnesium and calcium). Preferred anionic salts include the halides (such as chloride) salts.

A "biohydrolyzable ester" is an ester of the cyclic urethane compounds that does not interfere with the antiarrhythmic activity of the compounds, or that is readily metabolized by a human or other mammal to yield an antiarrhythmically-active cyclic urethane. Many such esters are known in the art, as described in World Patent Publication 87/05297, Johnston et al., published Sep. 11, 1987, and hereby incorporated by reference herein. Such esters include lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters).

As defined above and as used herein, substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thiol, aryl, cycloalkyl, heteroaryl, heterocycloalkyl (e.g., piperidinyl, morpholinyl, piperazinyl, pyrrolidinyl, etc.), imino, thioxo, hydroxyalkyl, aryloxy, arylalkyl, and combinations thereof.

DETAILED DESCRIPTION OF THE PRESENT INVENTION

The present invention encompasses certain novel cyclic urethanes, methods for their manufacture, and pharmaceutical compositions containing said novel compounds. In addition, the present invention relates to a method of treatment for cardiac arrhythmias and/or cardiac fibrillation in humans or other mammals utilizing amino-substituted cyclic urethanes, such as the novel cyclic urethane compounds of the present invention and cyclic urethanes as defined herein. Specific compounds and compositions to be used in the invention must, accordingly, be pharmaceutically-acceptable. As used herein, such a "pharmaceutically-acceptable" component is one that is suitable for use with humans and/or other mammals without undue adverse side effects (such as toxicity, irritation, and allergic response) commensurate with a reasonable benefit/risk ratio.

NOVEL CYCLIC URETHANE COMPOUNDS

The novel amino-substituted cyclic urethane compounds described hereinbelow are useful in treating cardiac arrhythmias and/or cardiac fibrillation in humans or other mammals and have the following general structure:

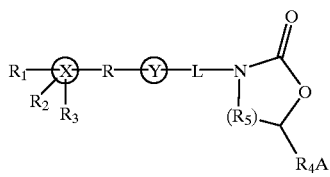

wherein
(a) X is a saturated or unsaturated, 5-, 6-, or 7-membered heterocycle or carbocycle;
(b) R is selected from the group consisting of covalent bond, nil, heteroatom, carboxyl, heterocyclic ring, carbocycle, alkyl, alkenyl, alkoxy, alkylamino, arylalkyl, acyl, aryloxy, acyloxy, and acylamino;
(c) Y is a substituted or unsubstituted, saturated or unsaturated, 5-, 6-, or 7-membered heterocycle or carbocycle, or is nil;
and wherein when R is nil, X and Y are fused ring systems; and when R is a covalent bond, X and Y are ring systems linked through a covalent bond; and when Y is nil, R is a covalent bond and X is a carbocycle ring bound to L through
(d) $R_1$, $R_2$, and $R_3$ are independently selected from the group consisting of nil, Cl, F, Br, $NH_2$, $CF_3$, OH, $SO_3H$, $CH_3SO_2NH$, COOH, alkoxy, alkyl, alkoxycarbonyl, hydroxyalkyl, carboxyalkyl, aminoalkyl, acylamino and acyloxy;
(e) L is selected from the group consisting of alkylamino, alkenylamino, alkylimino, alkenylimino, and acylamino; wherein the nitrogen atom of L is bound to the nitrogen atom at the 3-position of the cyclic urethane ring moiety;
(f) $R_4$ is selected from the group consisting of alkyl, alkenyl, alkynyl, alkylacyl, and heteroalkyl;
(g) A is a substituted or unsubstituted, saturated or unsaturated, straight-chain or branched $C_1$–$C_8$ heteroalkyl; or a substituted or unsubstituted, saturated or unsaturated 6-, or 7-membered heterocycle which may not have an oxygen; and A has at least one nitrogen atom adjacent to $R_4$; and
(h) $R_5$ is a substituted or unsubstituted $C_1$ or $C_2$ alkyl; and the pharmaceutically acceptable salts and esters thereof.

The Ring System (X-R-Y)

The novel cyclic urethane compounds of the present invention are useful for treating cardiac arrhythmia and/or cardiac fibrillation, and are comprised of a cyclic urethane moiety connected to a ring system (X-R-Y) via a linking moiety (L). The cyclic urethanes have a nitrogen atom at the 3-position, and an oxygen atom at the 1-position; the cyclic urethanes are substituted at the 5-position (when the cyclic urethane moiety is a 5-membered ring [$R_5=C_1$ alkyl]) and at the 6-position (when the cyclic urethane is a 6-membered ring [$R_5=C_2$ alkyl]), with an amino-containing moiety (A) separated from the carbon atom by a spacing group ($R_4$).

The ring system (X-R-Y) is a ring-containing moiety and consists of one carbocycle or two or more, fused or unfused, saturated or unsaturated, substituted or unsubstituted, rings as defined herein. Accordingly, the ring system may be monocyclic (Y is nil) or polycyclic (both X and Y are rings or all of X, R, and Y are rings). When there is only one ring, the ring is a carbocycle. When there are two or more rings, the rings may be carbocycles and/or heterocycles and each ring may be either a carbocycle or a heterocycle, and may contain 5, 6, or 7, preferably 5 or 6, members.

It is preferable that the ring system is polycyclic and is comprised of two, unfused rings. It is more preferable that the ring (Y) adjacent to the linking moiety (L) is a heterocycle, most preferably a five-membered ring which contains an oxygen atom at the 1-position. In addition, when there are two rings in the ring system, it is preferable that the heterocycle (Y) is covalently bound (through R) to the other ring (X) at the 5-position of the heterocycle Y and at the 1-position of ring X, and that heterocycle Y is bound to the carbon-containing end of the L moiety at the 2-position of heterocycle Y.

Although not preferred, it is acceptable for the ring system to be a polycyclic ring system comprised of two rings (X and Y) which are separated by an alkyl, a carbonyl, or a heteroatom, preferably oxygen (R). In addition, a suitable ring system might include a polycyclic ring system comprised of two rings (X and Y) which are fused (R is nil) or three rings (X, R, and Y) which are fused. When R is a ring, it is preferably a 5- or 6-membered carbocycle or heterocycle.

A particularly suitable ring system is monocyclic, and consists of only one carbocycle (X) which is covalently bound to the carbon-containing portion of L (R is covalent and Y is nil). However, when there is only one ring in the ring system, it is preferable that the ring be a 6-membered carbocycle, which is more preferably substituted with at least two, and most preferably with at least three, substituents independently chosen from the group consisting of, but not limited to hydroxy, methyl, chloro, methoxy, and benzoyl.

When substituted, any or all of the members of the ring system, whether monocyclic or polycyclic, may have one or more substituents. Said substituents may be independently selected from the group consisting of, and not limited to, Cl, F, Br, $NH_2$, $CF_3$, OH, $SO_3H$, $CH_3SO_2NH$, COOH, alkoxyl, alkoxycarbonyl, hydroxylalkyl, alkyl, aminoalkyl, acylamino, acyloxy and carboxyalkyl, especially Cl, F, Br, OH, and $CH_3$.

Preferred ring systems (X-R-Y) of the novel cyclic urethanes defined herein include, but are not limited to:

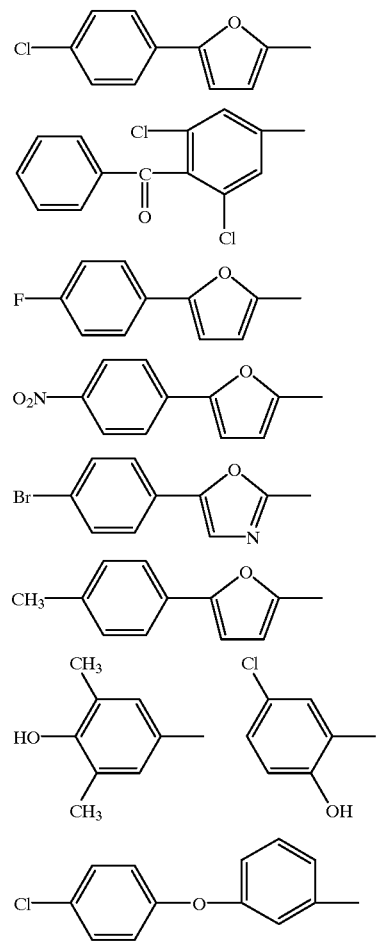

Preferred ring systems of the novel cyclic urethanes of the present invention which are useful for the treatment of cardiac arrhythmia and/or fibrillation include, but are not limited, for example, to monocyclic rings including, but not limited to,: 2-acetoxy-5-chlorophenyl; 3-hydroxy-5-hydroxymethyl-2-methyl-4-pyridinyl; 2-thienyl; 4-pyrimidinyl; cyclohexyl; 5-chloro-2-hydroxyphenyl; 5-chloro-2-methoxyphenyl; 2-methanesulfonylaminophenyl; 3-aminophenyl; 2-methoxyphenyl; 3-methoxy-phenyl; 2-aminophenyl; and 3,5-dimethyl-4-hydroxyphenyl. Suitable polycyclic ring systems which consist of two unfused rings, covalently bound to one another include, for example, but are not limited to, 5-(4-carboxyphenyl)-2-furanyl; 5-(4-methanesulfonylphenyl)-2-furanyl; 5-(3,4-dimethoxyphenyl)-2-furanyl; 5-(4-methanesulfonylaminophenyl)-2-furanyl; 5-(4-bromophenyl)-2-oxazolyl; 5-(4-methoxyphenyl)-2-furanyl; 5-(1-cyclohexen-1-yl)-2-furanyl; 5-cyclohexyl-2-furanyl; 5-(3-trifluoromethylphenyl)-2-furanyl; 5-(4-methylphenyl)-2-furanyl; 2-(4-chlorophenyl)-3-furanyl; 5-(4-chlorophenyl)-2-furanyl; 5-(4-fluorophenyl)-2-furanyl. Suitable polycyclic ring systems which consists of two unfused rings each connected to one another via a heteroatom, alkyl, or other non-cyclic carbon-containing group include, for example, but are not limited to, 2-benzyloxy-5-chlorophenyl; 4-benzyloxyphenyl; 3-(4-t-butylphenyloxy)phenyl; 3-benzyl-2,4-dichlorophenyl; 2-chloro-3-benzyloxyphenyl; 3-(4-chlorophenoxy)phenyl.

Suitable polycyclic ring systems containing two or more fused rings include, for example, but are not limited to, 1H-indol-3-yl; 2-fluorenyl; 2-naphthyl; 2-hydroxy-1-naphthyl; 2-quinolinyl; 5-chloro-2-benzofuranyl.

The Linking Moiety (L)

L is the linking moiety of the novel cyclic urethane compounds of the present invention. The carbon-containing end of L is bound to the X-R-Y ring system at Y, but if Y is nil, at X; most preferably at the 2-position of the Y ring or at the 1-position of X, if Y is nil. The nitrogen atom of the L moiety is bound to the nitrogen atom at the 3-position of the cyclic urethane moiety. The L moiety is selected from the group consisting of alkylamino, alkenylamino, alkylimino, alkenylimino, and acylamino, preferably alkylimino, most preferably a $C_1$ alkylimino, CH=N.

The Cyclic Urethane Moiety

The cyclic urethane moiety of the novel cyclic urethane compounds of the present invention gives the compounds described herein their characteristic name. The cyclic urethane moiety may be a 5- or 6-membered ring, preferably a 5-membered ring. The cyclic urethane moiety has the following structure:

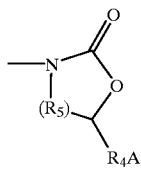

wherein $R_5$ is a $C_1$ or $C_2$ alkyl, preferably a $C_1$ alkyl. When $R_5$ is a $C_1$ alkyl, the cyclic urethane is a 5-membered ring and when $R_5$ is a $C_2$ alkyl, the cyclic urethane is a 6-membered ring.

A is a straight chain or branched, substituted or unsubstituted, saturated or unsaturated $C_1$–$C_8$ heteroalkyl or a substituted or unsubstituted, saturated or unsaturated 6-, or 7-, preferably a 6-, membered heterocyclic ring. A must have one nitrogen atom adjacent to $R_4$. When A is a heterocycle, A may contain nitrogen or sulfur heteroatoms, but may not contain an oxygen heteroatom.

When A is a substituted heteroalkyl, it is preferable that the substituents are selected from the group consisting of, but not limited to, methyl, hydroxyethyl, alkyl, aryl, heterocycle, arylalkyl, mercaptoethyl, and methanesulfonyl.

When A has two nitrogen atoms, it is preferable that the nitrogen atom not adjacent to $R_4$ (which in the case of a 6-membered heterocycle is para to the nitrogen atom adjacent to $R_4$) is substituted with substituents selected from the group consisting of, but not limited to, methyl, hydroxyethyl, alkyl, aryl, mercaptoethyl, methanesulfonyl, heterocycle, and arylalkyl. When heterocycle A has only one nitrogen atom, and A is a 6-membered ring, the position para to the nitrogen atom which next to $R_4$ is preferably substituted with substituents selected from the group consisting of, but not limited to, hydroxyethyl, hydroxy, oxo, and methyl.

Preferred A moieties of the novel cyclic methane compounds of the present invention include, but are not limited to:

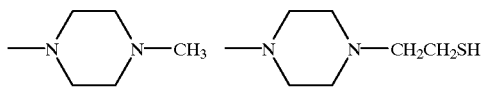

-continued

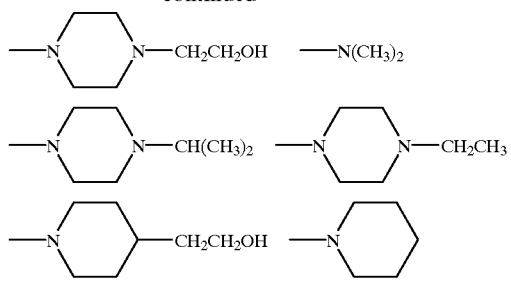

Accordingly, suitable A moieties of the novel cyclic urethane compounds of the present invention may include, but are not limited to, the following: Moieties where A is a heteroalkyl include, but are not limited to, dimethylamino; diethylamino; bis-2-hydroxyethylamino; bis-[(1-methyl)ethyl]amino; N-benzyl-N-methylamino; N-(2-hydroxyethyl)-N-methylamino. Suitable A moieties where A is a heterocycle include, but are not limited to N-(1-methylethyl)-N-[2-hydroxy-2-[(4-methanesulfonylamino)phenyl]ethyl]amino; 4-phenyl-1-piperazinyl; 4-(2-hydroxyethyl)- 1-piperazinyl; 4-[(1-methyl)ethyl]-1-piperazinyl; 4-(2-methyl)propyl-1-piperazinyl; 4-hexyl-1-piperazinyl; 4-benzyl-1-piperazinyl; 1-piperazinyl; 4-hydroxy-1-piperidinyl; 4-methyl-1-piperazinyl; 4-n-butyl-1-piperazinyl; 4-ethyl-1-piperazinyl; 3-(4-methyl-1-piperazinyl)-3-oxopropyl; 4-phenyl-1-piperazinyl; N-(2-pyridinyl)-1-piperazinyl; N-(2-pyrimidinyl)-1-piperazinyl; 4-(4-methoxyphenyl)-1-piperazinyl; 4-acetyl-1-piperazinyl; N-methyl-N-phenylamino; 4-(2-methylphenyl)-1-piperazinyl; 4-(4-methanesulfonylamino)-1-piperazinyl; N-thiomorpholinyl; 4-oxo-1-piperidinyl; 2-(t-butoxycarbonyl)-4-(4-acetylphenyl)-1-piperazinyl; hexahydro-1H-azepin-1-yl.

$R_4$ is connected to the cyclic urethane moiety at the 5-position (when the cyclic urethane moiety is a 5-membered ring) and at the 6-position (when the cyclic urethane moiety is a 6-membered ring) of the cyclic urethane moiety, and to a nitrogen atom of the A moiety. $R_4$ is selected from the group consisting of, and not limited to, alkyl, alkenyl, alkynyl, alkylacyl, and heteroalkyl, especially $C_3$–$C_6$ alkyls, i.e. propyl, butyl, pentyl, and hexyl.

As stated hereinabove, the cyclic urethane compounds of the present invention are comprised of a cyclic urethane moiety connected to a ring system via a linking moiety. Accordingly, the preferred cyclic urethane compounds of the present invention include, but are not limited to, the following compounds, and the hydrochloride salts thereof:

3-[[[5-(4-chlorophenyl)-2-furanyl]methylene]amino]-5-(1-piperidinylmethyl)-2-oxazolidinone;

3-[[[5-(4-chlorophenyl)-2-furanyl]methylene]amino]-5-[3-(1-piperidinyl)propyl]-2-oxazolidinone;

3-[[[5-(4-chlorophenyl)-2-furanyl]methylene]amino]-5-[4-(4-methyl-1-piperazinyl))butyl]-2-oxazolidinone;

3-[[[5-(4-chlorophenyl)-2-furanyl]methylene]amino]-5-[3-(4-methyl-1-piperazinyl)propyl]-2-oxazolidinone;

3-[[[5-(4-chlorophenyl)-2-furanyl]methylene]amino]-5-[[4-(2-hydroxyethyl)-1-piperidinyl]methyl]-2-oxazolidinone;

3-[[[5-(4-chlorophenyl)-2-furanyl]methylene]amino]-5-[(4-methyl-1-piperazinyl)methyl]-2-oxazolidinone.

Pharmaceutical Compositions Containing Novel Cyclic Urethane Compounds

The novel cyclic urethane compounds of the present invention may be administered to humans or other mammals by a variety of routes, including, but not limited to, oral dosage forms, and injections (intravenous, intramuscular, subcutaneous, and intraperitoneal). Numerous other dosage forms containing the novel cyclic urethane compounds of the present invention can be readily formulated by one skilled in the art utilizing the suitable pharmaceutical excipients as defined below. For considerations of patient compliance, oral dosage forms are generally most preferred.

The term "pharmaceutical composition" means a combination comprised of a safe and effective amount of a cyclic urea active ingredient, or mixtures thereof, and pharmaceutically-acceptable excipients.

The phrase "safe and effective amount", as used herein, means an amount of a compound or composition large enough to significantly positively modify the symptoms and/or condition to be treated, but small enough to avoid serious side effects (at a reasonable benefit/risk ratio), within the scope of sound medical judgment. The safe and effective amount of active ingredient for use in a pharmaceutical composition or in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular cyclic urethane active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be systemically administered to a human or other mammal, via delivery of a solution or emulsion containing the active ingredient, by puncturing the skin of said individual, in order to deliver said solution or emulsion to the circulatory system of the individual either by intravenous, intramuscular, subcutaneous, or intraperitoneal injection.

The rate of systemic delivery can be satisfactorily controlled by one skilled in the art, by manipulating any one or more of the following:

(a) the active ingredient proper;
(b) the pharmaceutically-acceptable excipients; so long as the variants do not interfere with the activity of the particular active ingredient selected;
(c) the type of the excipient, and the concomitant desirable thickness and permeability (swelling properties) of said coating;
(d) the time-dependent conditions of the excipient itself and/or within the excipients;
(e) the particle size of the granulated active ingredient; and
(f) the pH-dependent conditions of the excipients.

In particular, the solubility, acidity, and susceptibility to hydrolysis of the different cyclic urethane active ingredients, such as acid addition salts, salts formed with the carboxylic group, e.g., alkali metal salts, alkaline earth metal salts, etc., and esters, e.g., alkyl, alkenyl, aryl, arylalkyl, may be used as guidelines for the proper choice. In addition, suitable pH-conditions might be established within the oral dosage forms by adding a suitable buffer to the active ingredient in accordance with the desired release pattern.

As stated hereinabove, pharmaceutically acceptable excipients include, but are not limited to, resins, fillers, binders, lubricants, solvents, glidants, disintegrants cosolvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences,* 18th Edition, Mack Publishing Company, 1990, pp. 1288–1300, incorporated by reference herein. The pharmaceutical compositions suitable for use herein generally contain from 0–2% flavoring agents.

Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein. The pharmaceutical compositions herein generally contain from 0–2% dyes or pigments.

Preferred co-solvents include, but are not limited to, ethanol, glycerin, propylene glycol, polyethylene glycols. The pharmaceutical compositions of the present invention include from about 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred are phosphoric, tartaric, citric, and acetic acids and salts. The pharmaceutical compositions of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical composition of the present invention include 0–2% surfactants.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 1–10% binders.

Accordingly, the pharmaceutical compositions of the present invention include from 15–95% of a cyclic urethane compound active ingredient, or mixture thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

Suitable pharmaceutical compounds are described herein in Examples G–K. It is well within the capabilities of one skilled in the art to vary the non-limiting examples described herein to achieve a broad rank of pharmaceutical compositions.

Method of Treating Arrhythmias with Cyclic Urethane Compounds

The cyclic urethane compounds described herein are efficacious in treating humans or other mammals afflicted with supraventricular arrhythmias and ventricular arrhythmias and/or cardiac fibrillation. The novel compounds described herein are useful in treating cardiac arrhythmia and fibrillation; in addition, the amino-substituted cyclic urethane compounds described in the following U.S. Patents, all incorporated by reference herein, are also useful for treating cardiac arrhythmia and fibrillation: U.S. Pat. No. 2,798,068 to Gever, (assigned to The Norwich Pharmacal Company) issued Jul. 2, 1957; U.S. Pat. No. 2,802,002 to Gever, (assigned to The Norwich Pharmacal Company), issued Aug. 6, 19857, U.S. Pat. No. 3,318,878 to Dunn, (assigned to Smith Kline & French Laboratories), issued May 9, 1967; and U.S. Pat. No. 4,393,204 to Pelosi (assigned to Norwich Eaton Pharmaceuticals, Inc.) issued Jul. 12, 1983.

As stated hereinabove, except in rare cases, supraventricular arrhythmias are not deemed to be life threatening and are generally not aggressively treated with conventional antiarrhythmic drugs due to their undesirable side effects. Accordingly, this type of arrhythmia is usually not aggressively treated to merely relieve symptoms which are characterized as mild to severe. However, the compounds described herein generally exhibit less of many of the undesirable severe side effects than do many of the conventional antiarrhythmic drugs and, accordingly, may well be an acceptable therapy for individuals who are, in fact, experiencing discomfort, even though not in a life-threatening situation.

As stated hereinabove, the amino-substituted cyclic urethane compounds described herein are also effective in treating ventricular arrhythmias, which are, as a rule, much more serious than atrial arrhythmias and, accordingly, require aggressive therapy. Because of the seriousness of ventricular arrhythmias, many patient-type classifications have arisen. (See, e.g. cite to Thomas-Moore individual who characterized "prognostically significant").

Individuals suffering from benign ventricular arrhythmias are, from a philosophical standpoint of whether-to-treat, similar to those individuals experiencing supraventricular arrhythmias. These individuals do not have heart disease and may experience syncope, dizziness, and palpitations, and often suffer from a certain amount of emotional distress stemming from uncertainty caused by their physical symptoms. These individuals generally suffer from PVCs which are, for the most part, physically harmless, but understandably give rise to some degree of anxiety. The cyclic urethane compounds described herein generally exhibit less of the undesirable side effects which have made undesirable treatment of these individuals with many of the conventional antiarrhythmic drug, heretofore reserved for more serious life-threatening disease states. However, these individuals would likely benefit from therapy which is generally better tolerated.

Another class of individuals who may benefit from therapy utilizing the cyclic urethane compounds described herein are those individuals who are characterized as suffering from "prognostically-significant" arrhythmias. These individuals generally have suffered myocardial infarction and may have PVCs and/or episodes of non-sustained ventricular tachyarrhythmia, either symptomatic and asymptomatic. They do not exhibit the same degree of immediate, urgent life-threatening symptoms as do the individuals to be described hereinbelow and are not, by conventional characterization, in danger of immediate- or near-death. They are, however, at a significantly greater risk of sudden death than the general populace, and, accordingly, would be at a lessened risk of coronary failure with therapy utilizing the cyclic urethane compounds described herein.

Other individuals exist who continually exhibit life-threatening arrhythmias and are in danger of immediate or near-death. In these individuals, there is generally exhibited sustained ventricular tachyarrhythmia or ventricular fibrillation. The ventricular arrhythmias in these individuals generally produce hemodynamically significant signs or symptoms such as syncope, heart failure, myocardial ischemia or hypotension. These patients have the highest risk of sudden cardiac death and usually the most severe form of underlying cardiac disease. See *Morganroth & Bigger* at p. 1498 The cyclic urethanes described herein and pharmaceutical compositions thereof are effective, aggressive antiarrhythmic therapy suitable for use in this class of individuals, but with less of some the undesirable side effects heretofore generally tolerated with conventional antiarrhythmias, out of necessity and the unavailability of a suitable alternative to treat the life-threatening arrhythmias.

As stated above, the cyclic urethane compounds described herein exhibit less of many of the undesirable side effects associated with many conventional antiarrhythmic therapies. These side effects include, but are not limited to, pulmonary toxicity, cardiac depression, and neurological effects nonspecific to the cardiac tissue.

In addition, the cyclic urethane compounds described herein are antifibrillatory as well as antiarrhythmic; they prevent sudden cardiac death by uniformly prolonging the unexcitable period of the heart during each heartbeat. Conventional therapies exhibit anesthetic and/or cardiac depressive properties which merely make the heart less responsive, not less fibrillatory.

The amino-substituted cyclic urethane compounds described herein useful in treating cardiac arrhythmias and/or cardiac fibrillation in humans or other mammals. Accordingly, the present invention relates to a method for treating a human or other mammal suffering from cardiac arrhythmia and/or cardiac fibrillation which comprises administering to said human or other mammal a safe and effective amount of a pharmaceutical composition comprising from 15–90% of a cyclic urethane compound having the general formula:

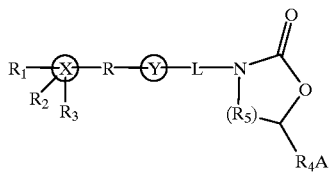

wherein (a) X is a saturated or unsaturated, 5-, 6-, or 7-membered heterocycle or carbocycle;

(b) R is selected from the group consisting of covalent bond, nil, heteroatom, carboxyl, heterocyclic ring, carbocycle, alkyl, alkenyl, alkoxy, alkylamino, arylalkyl, acyl, aryloxy, acyloxy, and acylamino;

(c) Y is a substituted or unsubstituted, saturated or unsaturated, 5-, 6-, or 7-membered heterocycle or carbocycle, or is nil;

and wherein when R is nil, X and Y are fused ring systems; and when R is a covalent bond, X and Y are ring systems linked through a covalent bond; and when Y is nil, R is a covalent bond and X is bound to L through R;

(d) $R_1$, $R_2$, and $R_3$ are independently selected from the group consisting of nil, Cl, F, Br, $NH_2$, $CF_3$, OH, $SO_3H$, $CH_3SO_2NH$, COOH, alkoxy, alkyl, alkoxycarbonyl, hydroxyalkyl, carboxyalkyl, aminoalkyl, acylamino and acyloxy;

(e) L is selected from the group consisting of alkylamino, alkenylamino, alkylimino, alkenylimino and acylamino; wherein the nitrogen atom of L is bound to the nitrogen atom at the 3-position of the cyclic urethane ring moiety;

(f) $R_4$ is selected from the group consisting of alkyl, alkenyl, alkynyl, alkylacyl, and heteroalkyl;

(g) A is a substituted or unsubstituted, saturated or unsaturated, straight-chain or branched $C_1$–$C_8$ heteroalkyl or a substituted or unsubstituted, saturated or unsaturated, 5-, 6-, or 7 membered heterocycle; and has one nitrogen atom adjacent to $R_4$; and (h) $R_5$ is a substituted or unsubstituted $C_1$ or $C_2$ alkyl, or the pharmaceutically-acceptable salts and esters thereof;

and 10–85% pharmaceutically-acceptable excipients.

The Ring System (X-R-Y)

The cyclic urethane compounds described herein which are useful as a method of treatment for cardiac arrhythmia and/or cardiac fibrillation are comprised of a cyclic urethane moiety connected to a ring system (X-R-Y) via a linking moiety (L). The cyclic urethanes have a nitrogen atom at the 3-position, and an oxygen atom at the 1-position, and are substituted with an amino-containing group (A) separated from the carbon atom of the cyclic urethane moiety by a spacing group ($R_4$).

The ring system (X-R-Y) is a ring-containing moiety and consists of one or more, preferably one or two, fused or unfused, saturated or unsaturated, substituted or unsubstituted, rings as defined herein. Accordingly, the ring system may be monocyclic (Y is nil) or polycyclic (both X and Y are rings or all of X, R, and Y are rings). Each ring may be either a carbocycle or a heterocycle, and may contain 5, 6, or 7, preferably 5 or 6, members.

It is preferable that the ring system is polycyclic and is comprised of two, unfused rings. It is more preferable that the ring (Y) adjacent to the linking moiety (L) is a heterocycle, most preferably a five-membered ring contains an oxygen atom at the 1-position. In addition, when there are two rings in the ring system, it is preferable that the heterocycle (Y) is covalently bound (through R) to the other ring (X) at the 5-position of the heterocycle Y and at the 1-position of ring X, and that heterocycle Y is bound to the carbon-containing end of the L moiety at the 2-position of heterocycle Y.

Although not preferred, it is acceptable for the ring system to be a polycyclic ring system comprised of two rings (X and Y) which are separated by an alkyl, a carbonyl, or a heteroatom, preferably oxygen (R). In addition, a suitable ring system might include a polycyclic ring system comprised of two rings (X and Y) which are fused (R is nil) or three rings (X, R, and Y) which are fused. When R is a ring, it is preferably a 5- or 6-membered carbocycle or heterocycle.

A particularly suitable ring system is monocyclic, and consists of only one carbocycle (X) which is covalently bound to the carbon-containing portion of L (R is covalent and Y is nil). However, when there is only one ring in the ring system, it is preferable that the ring is a 6-membered carbocycle, which is more preferably substituted with at least two, and most preferably with at least three, substituents independently chosen from the group consisting of, but not limited to hydroxy, methyl, chloro, methoxy, and benzoyl.

When substituted, any or all of the members of the ring system, whether monocyclic or polycyclic, may have one or more substituents. Said substituents may be independently selected from the group consisting of, and not limited to, Cl, F, Br, $NH_2$, $CF_3$, OH, $SO_3H$, $CH_3SO_2NH$, COOH, alkoxyl, alkoxycarbonyl, hydroxylalkyl, alkyl, aminoakyl, acylamino, acyloxy and carboxyalkyl, especially Cl, F, Br, OH, and $CH_3$.

Preferred ring systems (X-R-Y) of the cyclic urethanes useful as a method of treatment for cardiac arrhythmia and/or fibrillation as defined herein include, but are not limited to:

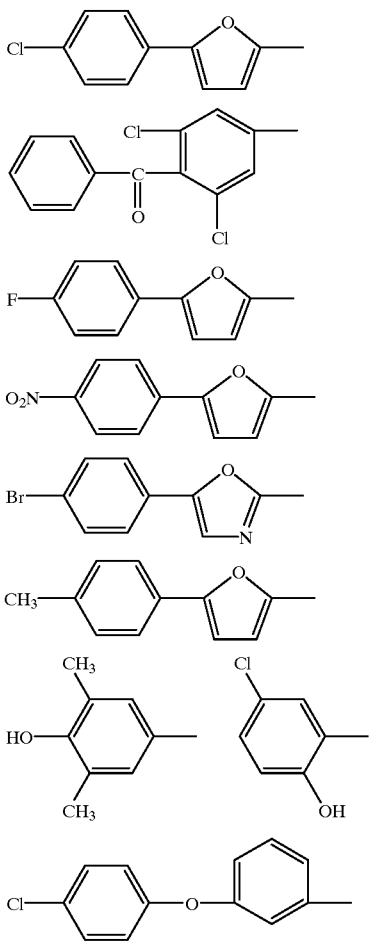

Preferred ring systems of the cyclic urethanes useful as a method of treatment for cardiac arrhythmia and/or fibrillation include, but are not limited, for example, to monocyclic rings including, but not limited to: 2-acetoxy-5-chlorophenyl; 3-hydroxy-5-hydroxymethyl-2-methyl-4-pyridinyl; 2-thienyl; 4-pyrimidinyl; 5-methoxycarbonyl-2-furanyl; cyclohexyl; 5-chloro-2-hydroxyphenyl; 5-chloro-2-methoxyphenyl; 2-methanesulfonylaminophenyl; 3-aminophenyl; 2-methoxyphenyl; 5-ethyl-2-furanyl; 3-methoxyphenyl; 2-aminophenyl; 3,5-dimethyl-4-hydroxyphenyl and 5-acetyloxymethyl-2-furanyl. Suitable polycyclic ring systems which consist of two unfused rings, covalently bound to one another include, for example, but are not limited to, 5-(4-carboxyphenyl)-2-furanyl; 5-(4-methanesulfonylphenyl)-2-furanyl; 5-(3,4-dimethoxyphenyl)-2-furanyl; 5-(4-methanesulfonylaminophenyl)-2-furanyl; 5-(4-bromophenyl)-2-oxazolyl; 5-(4-methoxyphenyl)-2-furanyl; 5-(1-cyclohexen-1-yl)-2-furanyl; 5-cyclohexyl-2-furanyl; 5-(3-trifluoromethylphenyl)-2-furanyl; 5-(4-methylphenyl)-2-furanyl; 2-(4-chlorophenyl)-3-furanyl; 5-(4-chlorophenyl)-2-furanyl; 5-(4-fluorophenyl)-2-furanyl. Suitable polycyclic ring systems which consists of two unfused rings each connected to one another via a heteroatom, alkyl, or other non-cyclic carbon-containing group include, for example, but are not limited to, 2-benzyloxy-5-chlorophenyl; 4-benzyloxyphenyl; 3-(4-t-butylphenyloxy)phenyl; 3-benzyl-2,4-dichlorophenyl; 2-chloro-3-benzyloxyphenyl; 3-(4-chlorophenoxyl) phenyl.

Suitable polycyclic ring systems containing two or more fused rings include, for example, but are not limited to, 1H-indol-3-yl; 2-fluorenyl; 2-naphthyl; 2-hydroxy-1-naphthyl; 2-quinolinyl; 5-chloro-2-benzofuranyl.

The Linking Moiety (L)

L is the linking moiety of the antiarrhythmic and antifibrillatory cyclic urethane compounds of the present invention. The carbon-containing end of L is bound to the X-R-Y ring system at Y, but if Y is nil, at X; most preferably at the 2-position of the Y ring or at the 1-position of X, if Y is nil. The nitrogen in the L moiety is bound to the nitrogen atom at the 1-position of the cyclic urethane moiety. The L moiety is selected from the group consisting of alkylamino, alkenylamino, alkylimino, alkenylimino, and acylamino, preferably alkylimino, most preferably a $C_1$ alkylimino, CH=N.

The Cyclic Urethane Moiety

The cyclic urethane moiety of the compounds useful as antiarrhythmic and antifibrillatory agents as described herein gives the compounds described herein their characteristic name. The cyclic urethane moiety may be a 5- or 6-membered ring, preferably a 5-membered ring. The cyclic urethane moiety has the following structure:

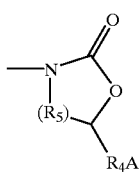

wherein $R_5$ is a $C_1$ or $C_2$ alkyl, preferably a $C_1$ alkyl. When $R_5$ is a $C_1$ alkyl, the cyclic urethane is a 5-membered ring and when $R_5$ is a $C_2$ alkyl, the cyclic urethane is a 6-membered ring.

A is a straight chain or branched, substituted or unsubstituted, saturated or unsaturated $C_1$–$C_8$ heteroalkyl or a substituted or unsubstituted, saturated or unsaturated 5-, 6-, or 7-, preferably a 6-, membered heterocyclic ring. The A moiety, whether a heteroalkyl or a heterocycle, must have at least one nitrogen atom which must be bound to $R_4$.

When A is a substituted heteroalkyl, it is preferable that the substituents are selected from the group consisting of, but not limited to, methyl, hydroxyethyl, alkyl, heterocycle, aryalkyl, mercaptoethyl, and methanesulfonyl. When heterocycle A has two nitrogen atoms, it is preferable that the nitrogen atom not adjacent to $R_4$ (which in the case of a 6-membered heterocycle is para to the nitrogen atom adjacent to $R_4$) is substituted with substituents selected from the group consisting of, but not limited to, methyl, hydroxyethyl, alkyl, aryl, mercaptoethyl, methanesulfonyl, heterocycle, and arylalkyl. When heterocycle A has only one nitrogen atom, and A is a 6-membered ring, the position para to the nitrogen atom which next to $R_4$ is preferably substituted with substituents selected from the group consisting of, but not limited to, hydroxyethyl, hydroxy, oxo, and methyl.

Preferred amine-containing (A) moieties of the cyclic urethanes useful as antiarrhythmic and antifibrillatory agents defined herein include, but are not limited to:

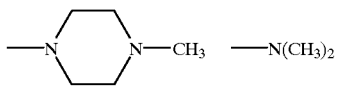

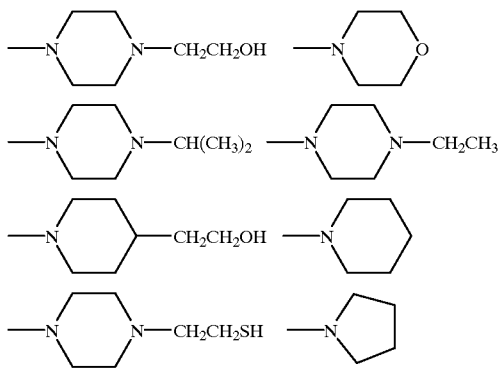

Suitable A moieties, accordingly, may include, but are not limited to, the following: Moieties where A is a heteroalkyl include, but are not limited to, dimethylamino; diethylamino; bis-2-hydroxyethylamino; bis-[(1-methyl)ethyl] amino; N-benzyl-N-methylamino; N-(2-hydroxyethyl)-N-methylamino. Suitable A moieties where A is a heterocycle include, but are not limited to 4-phenyl-1-piperazinyl; 4-(2-hydroxyethyl)-1-piperazinyl; 4-(1-methylethyl)-1-piperazinyl; 4-(2-methyl)propyl-1-piperazinyl; 4-hexyl-1-piperazinyl; 4-benzyl-1-piperazinyl; 1-piperazinyl; 4-hydroxy-1-piperidinyl; 4-methyl-1-piperazinyl; 4-n-butyl-1-piperazinyl; 4-ethyl-1-piperazinyl; 3-(4-methyl-1-piperazinyl)-3-oxopropyl; 4-phenyl-1-piperazinyl; N-(2-pyridinyl)-1-piperazinyl; N-(2-pyrimidinyl)-1-piperazinyl; 4-(4-methoxyphenyl)-1-piperazinyl; 4-acetyl-1-piperazinyl; N-methyl-N-phenylamino; 1-imidazolyl; 4-(2-methylphenyl)-1-piperazinyl; 4-(4-methanesulfonylamino)-1-piperazinyl; N-morpholinyl; N-thiomorpholinyl; 4-oxo-1-piperidinyl; 2-(t-butoxycarbonyl)-1-pyrrolidinyl; pyrrolidinyl; 4-(4-acetylphenyl)-1-piperazinyl; hexahydro-1H-azepin-1-yl.

$R_4$ is connected to the cyclic urethane moiety at the 5-position (when $R_5$ is a $C_1$ alkyl) or at the 6-position (when $R_5$ is a $C_2$ alkyl) of the cyclic urethane moiety and to a nitrogen atom of A. $R_4$ is selected from the group consisting of, but not limited to alkyl, alkenyl, alkynyl, alkylacyl, and heteroalkyl, especially $C_3$–$C_6$ alkyl, i.e. propyl, butyl, pentyl, and hexyl.

As stated hereinabove, the cyclic urethane compounds described herein are comprised of a cyclic urethane moiety connected to a ring system via a linking moiety. Accordingly, suitable compounds of the present invention include, but are not limited to, the following compounds, and the hydrochloride salts thereof: 3-[[[5-(4-chlorophenyl)-2-furanyl]methylene]amino]-5-(1-piperidinylmethyl)-2-oxazolidinone;
3-[[[5-(4-chlorophenyl)-2-furanyl]methylene]amino]-5-[3-(1- piperidinyl)propyl]-2-oxazolidinone;
3-[[[5-(4-chlorophenyl)-2-furanyl]methylene]amino]-5-[4-(4-methyl-1-piperazinyl))butyl]-2-oxazolidinone;
3-[[[5-(4-chlorophenyl)-2-furanyl]methylene]amino]-5-[3-(4-methyl-1-piperazinyl)propyl]-2-oxazolidinone;
3-[[[5-(4-chlorophenyl)-2-furanyl]methylene]amino]-5-[[4-(2-hydroxyethyl)-1-piperidinyl]methyl]-2-oxazolidinone;
3-[[[5-(4-chlorophenyl)-2-furanyl]methylene]amino]-5-[(4-methyl-1-piperazinyl)methyl]-2-oxazolidinone;
3-[[[5-(4-methylphenyl)-2-furanyl]methylene]amino]-5-(1-pyrrolidinylmethyl)-2-oxazolidinone;

The Examples M–S herein exhibit certain patient situations and illustrate the methods in which the cyclic urethane compounds described herein may be used to treat cardiac arrhythmias and fibrillation. It is well within the capabilities of one skilled in the art to vary the non-limiting examples described herein to treat a broad class of individuals suffering from cardiac arrhythmia and fibrillation.

The following examples will further serve to illustrate the present invention.

EXAMPLE A

Synthesis of 3-[[[5-(4-Chlorophenyl)-2-furanyl]methylene]-amino]-5-(1-piperidinylmethyl)-2-oxazolidinone Hydrochloride

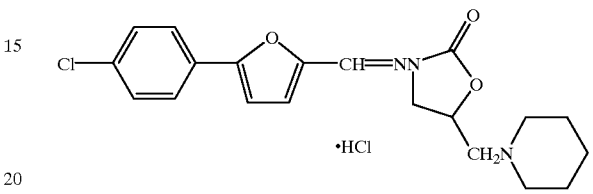

3-[[[5-(4-Chlorophenyl)-2-furanyl]methylene]-amino]-5-(1-piperidinylmethyl)-2-oxazolidinone hydrochloride is prepared as described below.

5-(4-Chlorophenyl)-2-furancarboxaldehyde [prepared as described in U.S. Pat. No. 4,882,354, to Huang et al. (assigned to Norwich Eaton Pharmaceuticals, Inc.,) issued Nov. 21, 1984; see cols. 7 & 8, hereby incorporated by reference] (3.92 g, 19.0 mmole) and 3-amino-5-(1-piperidinyl)methyl-2-oxazolidinone (3.78 g, 19.0 mole) [(prepared as described in U.S. Pat. No. 2,802,002 to Gever, (assigned to Norwich Eaton Pharmaceuticals, Inc. issued Aug. 6, 1957, see Example I, Part A, hereby incorporated by reference herein) in 150 ml of alcohol is treated with 3 ml of concentrated hydrochloric acid (pH ca. 3). The reaction mixture is stirred and heated at reflux for 2.5 hours. The mixture is chilled and filtered to give crude 3-[[[5-(4-chlorophenyl)-2-furanyl]methylene]amino]-5-(1-piperidinylmethyl)-2-oxazolidinone hydrochloride, which is purified by one recrystallization from nitromethane (activated charcoal) yielding 3.2 g.

EXAMPLE B

Synthesis of 3-[[[5-(4-Chlorophenyl)-2-furanyl]methylene]-amino]-5-[1-(4-methyl-1-piperazinyl)methyl]-2-oxazolidinone Dihydrochloride

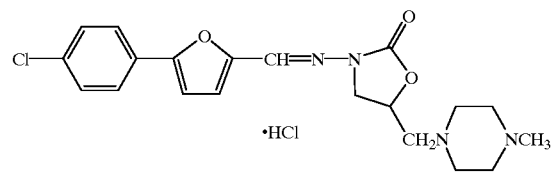

3-[[[5-(4-Chlorophenyl)-2-furanyl]methylene]-amino]-5-[1-(4-methyl-1-piperazinyl)methyl]-2-oxazolidinone dihydrochloride is prepared as described below.

I. Synthesis of 3-[(Phenylmethylene)amino]-5-]1-(4-methyl-1-piperazinyl)methyl]-2-oxazolidinone Hydrochloride A solution of 5-(chloromethyl)-3-[(phenylmethylene)amino]-2-oxazolidinone (prepared as described in "Stereospecific Synthesis of Some Optically Active 5-Substituted-3-Aralkylideneamino-2-oxazolidinones", By N. D. Harris, *J. Org. Chem.* Vol. 28, pp. 745–748 (1963) (hereby incorporated by reference herein); (5.0 g, 0.021 mole, dimethylformamide (50 ml) and N-methylpiperazine (25 ml) is heated to reflux. Reflux is maintained for 4 hours. The solution is concentrated under reduced pressure to an oily residue. The residue is dissolved in absolute ethanol (20 ml) and cooled on an ice bath. A solid separated and is collected and then air-dried to give 2 g of crude product. The filtrate is concentrated under reduced pressure, then under high vacuum at 55–60° C. A clear liquid is removed, leaving a wet solid residue. This residue is triturated with acetonitrile giving a solid. The solid is collected and partially air-dried. This solid is combined with the above crude product, triturated with acetonitrile (25 ml), collected and air-dried to give 4.05 g (0.012 mole) of intermediate.

II. Synthesis of 3-[[[5-(4-Chlorophenyl)-2-furanyl]methylene]-amino]-5-[1-(4-methyl-1-piperazinyl)methyl]-2-oxazolidinone A mixture of the intermediate synthesized in Part I above (4.05 g, 0.012 mole), 2N HCl (125 ml) and 5% Pd/C 50% $H_2O$ (1.0 g) is subjected to hydrogen on a Parr apparatus at 40 psi at ambient temperature. After 1 hour, the shaking is stopped. The catalyst is removed by filtration and the filtrate is concentrated under reduced pressure to an oily residue.

This residue is suspended in dimethylformamide, then added to a solution of 5-(4-chlorophenyl)-2-furancarboxaldehyde [prepared as described in U.S. Pat. No. 4,882,354 to Huang et al. (assigned to Norwich Eaton Pharmaceuticals, Inc.) issued Nov. 21, 1984; see cols. 7 and 8, hereby incorporated by reference herein] (2.5 g, 0.012 mole) in dimethylformamide (40 ml). The resulting solution is stirred at ambient temperature overnight. The solid is collected and partially air-dried. This solid is recrystallized by boiling in absolute ethanol, then adding, $H_2O$ to dissolve. After cooling on an ice bath, the solid is collected, air-dried and dried in vacuo at 100° C. to give 2.08 g (0.0044 mole) of 3-[[[5-(4-chlorophenyl)-2-furanyl]methylene]-amino]-5-[1-(4-methyl-1-piperazinyl)methyl]-2-oxazolidinone dihydrochloride.

EXAMPLE C

Synthesis of 3-[[[5-(4-Chlorophenyl)-2-furanyl]methylene]-amino]-5-[[4-(2-hydroxyethyl)-1-piperidinyl]methyl]-2-oxazo-lidinone Hydrochloride ml of dry dimethylformamide is treated with anhydrous sodium iodide (12.6 g, 0.08 mole) and warmed for 0.5 hour. The reaction solution is then treated with anhydrous potassium carbonate (5.8 g, 0.04 mole), followed by the addition of 4-piperidineethanol (5.43 g, 0.04 mole). The reaction mixture is heated at near reflux for 2 hours and is left to stand at ambient temperature for 6.0 hours. The reaction mixture is filtered and the filtrate is concentrated under reduced pressure to leave an oily residue. The residue is treated with 300 ml of $H_2O$ and extracted with 3×300 ml portions of ethyl acetate. The ethyl acetate extracts are combined and dried over anhydrous magnesium sulfate. The desiccant is removed and the filtrate concentrated under reduced pressure to give an amber oil.

The oil is taken up in absolute alcohol (100 ml) and treated with a saturated mixture of ethanolic/HCl. The reaction solution is stirred for 10 minutes to crystallize a light tan solid. The solid is collected and washed with anhydrous ether. The sample is next recrystallized from absolute alcohol (activated charcoal) to give 3-phenylmethyleneamino-5-[4-(2-hydroxyethyl)-1-piperidinyl)methyl]-2-oxazolidinone hydrochloride.

II. Synthesis of 3-[[[5-(4-Chlorophenyl)-2-furanyl]methylene]amino]-5-[[4-(2-hydroxyethyl)-1-piperidinyl]methyl]-2-oxazolidinone Hydrochloride A solution of the intermediate synthesis in Part I hereinabove (2.0 g, 0.006 mole) in 200 ml of 2N HCl is treated with 5% palladium on carbon [50% $H_2O$ (2.0 g)]. The reaction mixture is reduced on Parr apparatus under hydrogen. The hydrogen uptake is stopped after 0.5 hours, after 140% of theory is reached. The catalyst is removed and the filtrate concentrated under reduced pressure to leave an off-white residue. The residue is treated with a solution of 5-(4-chlorophenyl)-2-furancarboxaldehyde [prepared as described in U.S. Pat. No. 4,882,354 to Huang et al. (assigned to Norwich Eaton Pharmaceuticals, Inc.) issued Nov. 21, 1984; see cols. 7 and 8, hereby incorporated by reference herein] (1.21 g, 0.006 mole) in 50 ml of dry dimethylformamide. The reaction is stirred at ambient temperature overnight. The reaction mixture is filtered and washed with anhydrous ether to give 2.44 g of product. The resulting product is further purified by one recrystallization from absolute alcohol (small amt. of $H_2O$ added) (activated charcoal/Celite) to yield 1.4 g of 3-[[[5-(4-chlorophenyl)-2-

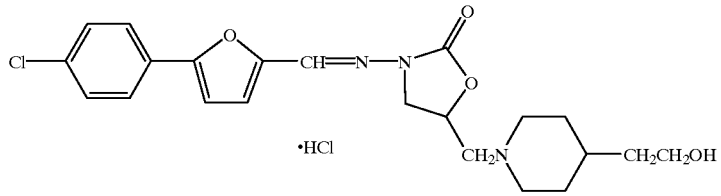

3-[[[5-(4-Chlorophenyl)-2-furanyl]methylene]-amino]-5-[[4-(2-hydroxyethyl)-1-piperidinyl]methyl]-2-oxazolidinone hydrochloride is prepared as described hereinbelow.

I. Synthesis of 3-Phenylmethyleneamino-5-[4-(2-hydroxyethyl)-1-piperidinyl)methyl]-4-2-oxazolidinone Hydrochloride A stirred solution of 5-(chloromethyl)-3-[(phenylmethylene)amino]-2-oxazolidinone, prepared as described in Part I of Example B (10.0 g, 0.04 mole) in 270 furanyl]methylene]-amino]-5-[[4-(2-hydroxyethyl)-1-piperidinyl]methyl]-2-oxazolidinone hydrochloride.

EXAMPLE D

Synthesis of 3-[[[5-(4-Chlorophenyl)-2-furanyl]methylene]amino]-5-[3-(1-piperidinyl)propyl]-2-oxazolidinone hydrochloride

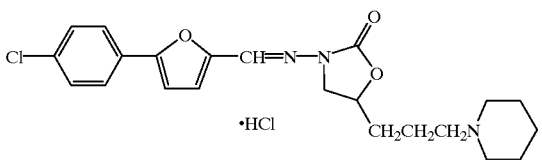

3-[[[5-(4-Chlorophenyl)-2-furanyl]methylene]amino]-5-[3-(1-piperidinyl)propyl]-2-oxazolidinone Hydrochloride is prepared as described hereinbelow.

I) Synthesis of solution containing meta-Chloroperoxybenzoic Acid

In a 5 liter, three-neck flask with a mechanical stirrer is placed H₂O (1000 ml), magnesium sulfate×7H₂O (5.77 g, 0.0234 mole), then sodium hydroxide (138.5 g, 3.46 mole). The resulting hazy solution is cooled by an ice bath to 10–15° C. 30% Hydrogen peroxide (340 ml) is added, followed by dioxane (1250 ml). While stirring vigorously at 10–15° C., 3-chlorobenzoyl chloride (200 g, 1.143 mole) is added by pouring a slow stream, keeping the temperature <28° C. The resulting mixture is cooled to 15–20° C. and stirred 30 minutes. While at 15° C., 20% H₂SO₄ (cooled, as much of 3100 ml as possible) was added while stirring. After 10 minutes the mixture is transferred to a 6 liter separatory funnel, adding the remaining 20% H₂SO₄. The organic layer is separated and the aqueous phase extracted with CH₂Cl₂ (2×500 ml, 4×250 ml). The combined organic layers are dried over MgSO₄. The filtered solution contains ~1.14 mole of 80–85% meta-chloroperoxybenzoic acid and is used.

II. Benzylidene Ethyl Carbazate Potassium Salt

A solution of ethyl carbazate (50.0 g, 0.480 mole), acetic acid (350 ml), and benzaldehyde (49 ml, 50.9 mg, 0.480 mole) is stirred 2 hours. The mixture is poured into H₂O (~3500 ml) which is stirred 1 hours. The solid is collected, washed with H₂O and air-dried. Drying is continued at 60° to give 85 g (0.4422 mole) of benzylidene ethyl carbazate.

Benzylidene ethyl carbazate (40.0 g, 0.2081 mole) is dissolved in absolute ethanol (500 ml). To this solution is added a solution of potassium t-butoxide (23.4 g, 0.2081 mole) in absolute ethanol (200 ml, prepared by portionwise addition, then cooling on ice) in one portion. The resulting mixture is stirred 1.5 hours at ambient temperature. The solid is collected, washed with anhydrous ether, and air-dried. Drying is continued at 60° C. to give 45.0 g (0.1954 mole) of benzylidene ethyl carbazate potassium salt.

III. Synthesis of 4-Penten-1-ol, Benzyl Ester

A stirred solution of 4-penten-1-ol (77 ml, 64.6 g, 0.75 mole) in dimethylformamide (800 ml) is treated with NaH, 60% in mineral oil (30.0 g, 0.75 mole) portionwise over ~2 hours. The temperature is maintained at 10–20° C. with mild ice bath cooling. After addition, the mixture is stirred 2 hours at ambient temperature, then heated at 80–90° C. for 2 hours After cooling to ambient temperature, the mixture is cooled to 5–10° C. While stirring at 5–10° C., benzyl chloride (86.3 ml, 0.75 mole) is added dropwise over approximately 45 minutes. Stirring is continued cold 1 hour, then at ambient temperature overnight. The mixture is heated at 80–90° C. for 3 hours, then cooled to ambient temperature. The mixture is concentrated under reduced pressure to an oily-solid residue. This residue is suspended in H₂O (400 ml), then extracted with ethyl ether (4×200 ml). The ether extract is washed with H₂O (4×150 ml), then dried over MgSO₄. The filtered solution is concentrated under reduced pressure by rotary evaporator to yield 4-penten-1-ol, benzyl ester (102 g, 0.579 mole) as a liquid residue.

IV. Synthesis of (4,5-Epoxy)pentan-1-ol, Benzyl Ester

A solution of meta-chloroperoxybenzoic acid (prepared according to Part I herein) containing ~1.14 mole of peracid in CH₂Cl₂ and dioxane is stirred and cooled to 0–5° C. 4-Penten-1-ol, benzyl ester, (prepared according to Part III herein) (102 g, 0.579 mole) is added dropwise at 0–5° C. over 1 hour. The solution is stirred cold and allowed to warm slowly to ambient temperature. Stirring is continued at ambient temperature for 5 days. The solution is washed with 1N NaOH (2×3500 ml, accomplished by washing in ⅓ portions). The organic layer is dried over MgSO₄. The filtered solution is concentrated under reduced pressure to a liquid residue, which is distilled in vacuo collecting the product of 95–120° C. at 1–0.5 mm Hg, giving 77.2 g (0.402 mole) of (4, 5-epoxy)pentan-1-ol, benzyl ester.

V. Synthesis of 5-[3-(Phenylmethoxy)propyl]-3-phenylmethylene-amino-2-oxazolidinone A stirred solution of benzylidene ethyl carbazate potassium salt as synthesized in Part II (34.0 g, 0.1476 mole), dimethylformamide (550 ml) and (4,5-epoxy)pentan-1-ol, benzyl ester as prepared according to Part IV herein (42.6 g, 0.2214 mole, 1.5 eq.) is heated to reflux. Reflux is maintained for 3 hours. After cooling, the mixture is concentrated under reduced pressure to an oily residue. This residue is dissolved in CH₂Cl₂ (500 ml), then washed with H₂O (4×200 ml), saturated NaCl solution. (1×200 ml), then dried over MgSO₄. The filtered solution is concentrated under reduced pressure to an oily residue. The residue is triturated in anhydrous ether (500 ml) by stirring 15 minutes. The solid is collected, washed with ether, and air-dried to give 27.1 g (0.0801 mole) of 5-[3-(phenylmethoxy)propyl]-3-phenylmethyleneamino-2-oxazolidinone.

VI. Synthesis of 3-Phenylmethyleneamino-5-(3-hydroxy)propyl-2-oxazolidinone

A mixture of 5-[3-(phenylmethoxy)propyl]-3-phenylmethylenamine-2-oxazolidinone (20.0 g, 0.0591 mole), 2N HCl (450 ml) and 5% Pd/C:50% H₂O (~5 g) is subjected to hydrogen on a Parr apparatus at 40 psi at ambient temperature. After ~2 hours, H₂ uptake is stopped at 100% of theory. The catalyst is removed by filtration and the filtrate is concentrated under reduced pressure to an oily residue.

The above reaction is repeated in an identical manner using 22.0 g (0.0650 mole) of 5-[3-(phenylmethoxy)propyl]-3-phenylmethenamino-2-oxazolidinone. Work-up gives an oily residue.

The above residues are combined (0.1241 mole), and are added to dimethylformamide (500 ml), benzaldehyde (13.17 g, 0.1241 mole) and molecular sieves (3 Angstrom) and the mixture is stirred at ambient temperature overnight. The sieves are removed by filtration and the filtrate is concentrated under reduced pressure to an oily residue. This residue is chromatographed on a Waters Prep 500 on normal phase silica gel, eluting with 2.5% MeOH/CH₂Cl₂. Fractions containing product are combined and concentrated under reduced pressure to a semi-solid residue. This residue is triturated in anhydrous ether (400 ml) by stirring for 30 minutes. The solid is collected and air-dried to give 23.68 g (0.0954 mole) of 3-phenylmethylenamino-5-($^3$-hydroxy)propyl-2-oxazolidinone.

VII. Synthesis of 5-(3-Chloropropyl)-3-phenylmethyleneamino-$^2$-oxazolidinone

A mixture of 3-phenylmethyleneamino-5-(3-hydroxy)propyl-2-oxazolidinone (10.88 g, 0.0438 mole) CHCl₃ (200 ml), and pyridine (4.25 ml, 4.16 g, 0.0526 mole, 1.2 eq.) is stirred at ambient temperature. Thionyl chloride (11.2 ml, 18.2 g, 0.1533 mole, 3.5 eq.) is added dropwise over 30–45 minutes while at ambient temperature (slight exotherm observed). After complete addition, the solution is heated to reflux. Reflux is maintained for 2 hours. After cooling, the solution is concentrated under reduced pressure to a solid residue, which is azeotroped with toluene (2×50 ml). The solid is dissolved in $CH_2Cl_2$ (250 ml), then washed with $H_2O$ (3×100 ml). The $CH_2Cl_2$ is dried over $MgSO_4$, filtered, then concentrated under reduced pressure to give 5-(3-chloropropyl)-3-phenylmethyleneamino-2-oxazolidinone (11.2 g, 0.0420 mole) as a solid residue.

VIII. Synthesis of 3-Phenylmethyleneamino-5-[3-(1-piperidinyl) propyl]-2-oxazolidinone A stirred solution of 5-(3-chloropropyl)-3-phenylmethyleneamino-2-oxazolidinone (2.7 g, 0.0101 mole), dimethylformamide (75 ml) and piperidine (2.15 g, 0.0253 mole, 2.5 eq.) is heated to reflux. Reflux is maintained for 2 hours. After cooling, the solution is concentrated under reduced pressure to a solid-oily residue. This residue is suspended in $H_2O$ (200 ml) then extracted with ethyl acetate (3×100 ml). The ethyl acetate is dried over $MgSO_4$, filtered, then concentrated under reduced pressure to an oily-solid residue. This residue is triturated in hexane by stirring 1 hours. The solid is collected and air-dried giving 1.67 g (0.0053 mole) of 3-phenylmethyleneamino-5-[3-(1-piperidinyl)propyl]-2-oxazolidinone.

IX. Synthesis of 3-[[[5-(4-Chlorophenyl)-2-furanyl]methylene]amino]-5-[3-(1-piperidinyl)propyl]-2-oxazolidinone Hydrochloride A mixture of 3-phenylmethyleneamino-5-[3-(1-piperidinyl)propyl]-2-oxazolidinone (1.67 g, 0.0053 mole), 2N HCl (125 ml) and 5% Pd/C:50% $H_2O$ (~2 g) is subjected to hydrogen on a Parr apparatus at 40 psi at ambient temperature. After 1 hour, hydrogen uptake is stopped at 100% of theory. The catalyst is removed by filtration. The filtrate is concentrated under reduced pressure to an oily residue, which is azeotroped with absolute ethanol (2×25 ml), giving a solid residue.

A solution of the above residue, dimethylformamide (50 ml) and 5-(4-chlorophenyl)-2-furancarboxaldehyde, [prepared as described in U.S. Pat. No. 4,882,354 to Huang et al. (assigned to Norwich Eaton Pharmaceuticals, Inc.) issued Nov. 21, 1984, see cols 7 & 8 hereby incorporated by reference herein] (1.10 g, 0.0053 mole) is stirred at ambient temperature overnight. The mixture is filtered, collecting a solid, which is recrystallized from absolute ethanol/$H_2O$ by boiling in absolute ethanol, then adding $H_2O$ until a solution is obtained. This is filtered, then cooled on ice. The solid is collected, air-dried, then dried under vacuum at 77° C. for 15 to 16 hours to give 1.14 g (0.0025 mole) of 3-[[[5-(4-chlorophenyl)-2-furanyl]methylene]amino]-5-[3-(1-piperidinyl)propyl]-2-oxazolidinone hydrochloride.

EXAMPLE E

Synthesis of 3-[[[5-(4-Chlorophenyl)-2-furanyl]methylene]amino]-5-[3-(4-methyl-1-piperazinyl) propyl]-2-oxazolidinone Dihydrochloride

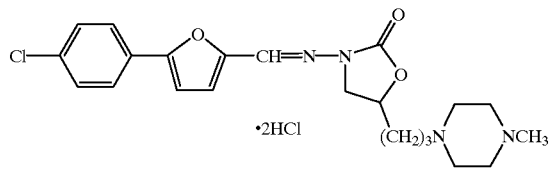

3-[[[5-(4-chlorophenyl)-2-furanyl]methylene]amino]-5-[3-(4-methyl-1-piperazinyl)propyl]-2-oxazolidinone dihydrochloride is prepared as described hereinbelow.

I. Synthesis of 5-(3-Chloropropyl)-3-phenylmethyleneamino-2-oxazolidinone 5-(3-Chloropropyl)-3-phenylmethyleneamino-2-oxazolidinone is prepared according to Example D, Parts I–VII.

II. Synthesis of 3-Phenylmethyleneamino-5-[3-(4-methyl-1-piperazinyl)propyl]-2-oxazolidinone A stirred solution of 5-(3-chloropropyl)-3-phenylmethylene-amino- 2-oxazolidinone (5.0 g, 0.0187 mole,), dimethylformamide (100 ml) and 1-methylpiperazine (5.62 g, 0.0561 mole) is heated to reflux. Reflux is maintained for 2.5 hours. After cooling, the dark solution is concentrated under reduced pressure to an oily residue. This residue is suspended in saturated $NaHCO_3$ (200 ml), and is extracted with $CH_2Cl_2$ (3×100 ml). The $CH_2Cl_2$ extract is washed with saturated $NaHCO_3$ (1×200 ml) then dried over $MgSO_4$. The filtered solution is concentrated under reduced pressure to a solid residue. This is triturated in hexane, collected and air-dried to give 4.97 g (0.0150 mole) of 3-phenylmethylene-amino-5-[3-(4-methyl-1-piperazinyl)propyl]-2-oxazolidinone.

III. 3-[[[5-(4-chlorophenyl)-2-furanyl]methylene]amino]-5-[3-(4-methyl-1-piperazinyl)propyl]-2-oxazolidinone Dihydrochloride A mixture of 3-phenylmethyleneamino-5-[3-(4-methyl-1-piperazinyl)propyl]-2-oxazolidinone (2.5 g, 0.0076 mole), 2N HCl (125 ml) and 5% Pd/C:50% $H_2O$ (2 g) is subjected to $H_2$ on a Parr apparatus at 40 psi at ambient temperature. After 2 hours, $H_2$ uptake ceases at 100% of theory. The catalyst is removed by filtration and the filtrate concentrated under reduced pressure to a gummy residue.

This residue, dimethylformamide (50 ml), and 5-(4-chlorophenyl)-2-furancarboxaldehyde [prepared as described in U.S. Pat. No. 4,882,354 to Huang et al. (assigned to Norwich Eaton Pharmaceuticals, Inc.) issued Nov. 21, 1984; see cols. 7 and 8, hereby incorporated by reference herein]; (1.57 g, 0.0076 mole) are stirred at ambient temperature overnight. The resulting solid is collected and air-dried. This solid is recrystallized from absolute ethanol and $H_2O$, then collected, next air-dried and dried in vacuo at ambient temperature to give 1.96 g (0.0039 mole) of 3-[[[5-(4-chlorophenyl)-2-furanyl]-methylene]amino]-5-[3-(4-methyl-1-piperazinyl)propyl]-2-oxazolidinone dihydrochloride.

EXAMPLE F

Synthesis of 3-[[[5-(4-Chlorophenyl)-2-furanyl]methylene]amino]-5-[4-(4-methyl-1-piperazinyl)butyl]-2-oxazolidinone Dihydrochloride

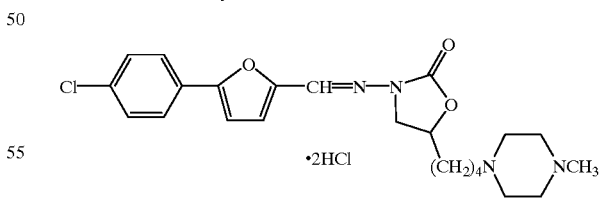

I. Synthesis of 5-Hexen-1-ol, Benzyl Ester

A stirred solution of 5-hexen-1-ol (75 g, 0.749 mole ) in dimethylformamide (800 ml) is treated with 60% NaH in mineral oil (30.0 g, 0.75 mole) portionwise over 1.5 hour while keeping the temperature 0–5° C. After complete addition, the mixture is stirred cold 1 hour, then heated at steam bath temperature (90° C.) for 2.5 hours. The brown mixture is cooled by an ice bath to 0–5° C. Benzyl chloride (87 ml, 0.75 mole) is added dropwise over 45 minutes keeping the temperature 0–5° C. After complete addition, the mixture is stirred at ambient temperature for 16 to 18 hours. The mixture is heated at 80–90° C. for 3.5 hour then cooled to ambient temperature. The mixture is concentrated under reduced pressure to an oily residue. This residue is suspended in $H_2O$ (500 ml) then extracted with ether (2×300 ml, 2×100 ml). The ether extract is washed with $H_2O$ (4×200 ml), dried over $MgSO_4$, filtered and then concentrated under reduced pressure to an oily-liquid residue containing the product ester (126 g, ~12 g is mineral oil giving ~114 g, 0.60 mole).

II. Synthesis of 5,6-Epoxyhexan-1-ol, Benzyl Ester

3-Chloroperoxybenzoic acid (500 g, ~4 eq., 50–60%) is dissolved in $CH_2Cl_2$ (3500 ml). The solution is dried over $MgSO_4$ and then filtered.

The clear filtrate is cooled by an ice bath to 5–10° C. To this is added 5-hexen-1-ol, benzyl ester (126 g, 0.60 mole) dropwise over 1.5 hour. The resulting mixture is stirred cold several hours, then allowed to warm to ambient temperature, and is next stirred another 16 hours. The mixture is washed with iN NaOH (2×2000 ml, 6×1000 ml), $H_2O$ (3×600 ml), saturated $NaHCO_3$ (1×600 ml), then dried over $MgSO_4$. The filtered solution is concentrated under reduced pressure to a liquid residue. The residue is distilled in vacuo, giving one major fraction collected at 100–120° C. at 0.5 mm Hg (70 g, 0.34 mole, 56% yield). A second distillation gives two fractions of 5,6-epoxyhexan-1-ol, benzyl ester, 16.1 g collected at 102–110° C. at 0.3 mm Hg and 31.9 g collected at 110–114° C. at 0.3 mm Hg (combined yield, 48 g, 0.233 mole). Each fraction is the desired product.

III. Synthesis of 5-[4-(Phenylmethoxy)butyl]-3-phenylmethylene-amino-2-oxazolidinone A stirred solution of benzylidene ethyl carbazate prepared as described in Example D, Part II (32.0 g, 0.1663 mole), benzylidene ethyl carbazate potassium salt prepared as described in Example D, Part II (2.03 g, 0.0088 mole) 5,6-epoxyhexan-1-ol, benzyl ester (38 g, 0.1842 mole) and dimethylformamide (800 ml) is heated to reflux. Reflux is maintained for about 2.5 hours then cooled to ambient temperature. The solution is concentrated under reduced pressure to an oily residue. This residue is dissolved in $CH_2Cl_2$ (500 ml), then washed with $H_2O$ (4×200 ml), saturated NaCl (2×200 ml), dried over $MgSO_4$ (activated charcoal), filtered and concentrated under reduced pressure to an oily residue. This residue is diluted with anhydrous ether (600 ml) and stirred 2 hours. The precipitated solid is collected, washed with anhydrous ether, and then air-dried to give 38.18 g (0.1083 mole) of 5-[4-(phenylmethoxy)butyl]-3-phenylmethyleneamino-2-oxazolidinone.

IV. Synthesis of 3-Phenylmethyleneamino-5-(4-hydroxybutyl-2-oxazolidinone

A mixture of 5-[4-(phenylmethoxy)butyl]-3-phenylmethylene amino-2-oxazolidinone (23.0 g, 0.0653 mole), 2N HCl (625 ml) and 5% Pd/C:50% $H_2O$ (~5 g) is subjected to H2 on a Parr apparatus at 40 psi at ambient temperature. After 2 hours, $H_2$ uptake ceases at 100% of theory. The catalyst is removed by filtration and the filtrate is recharged with fresh catalyst and hydrogenation is resumed as above. After 2 hours, no additional $H_2$ uptake is observed. The catalyst is removed by filtration and the filtrate is concentrated under reduced pressure to an oily residue.

This reaction is repeated in an identical manner in an identical scale, and combined with the above residue. This combined residue is azeotroped with absolute ethanol (4×50 ml) giving a semi-solid residue.

This residue, dimethylformamide (600 ml), benzaldehyde (13.9 g, 0.1305 mole), and 3.0 g of molecular sieves, (3 Angstrom), are stirred at ambient temperature overnight. The sieves are removed by filtration and the filtrate is next concentrated under reduced pressure to an oily residue which is partially crystallized upon standing to give 50.4 g of 3-phenylmethyleneamino-5-(4-hydroxybutyl)-2-oxazolidinone.

V. Synthesis of 5-(4-Chlorobutyl)-3-phenylmethyleneamino-2-oxazolidinone

Thionyl chloride (23.8 ml, 38.8 g, 03165 mole) is added dropwise over 1 hour to a stirred solution of 3-phenylmethylene-amino-5-(4-hydroxybutyl)-2-oxazolidinone (50.4 g, 0.1306 mole), $CHCl_3$ (600 ml) and pyridine (22.7 g, 0.2873 mole). After complete addition, the solution is heated to reflux. Reflux is maintained for 3.5 hours. After cooling, the solution is concentrated under reduced pressure to an oily residue. This residue is azeotroped with toluene (3×500 ml), giving a solid residue. This residue is dissolved in $CH_2Cl_2$ (500 ml), washed with $H_2O$ (4×200 ml), saturated NaCl (2×100 ml), next dried over $MgSO_4$, filtered, and then concentrated under reduced pressure to a solid residue. This residue is triturated in anhydrous ether (500 ml) by stirring several hours. The solid is collected, washed with ether, and air-dried to give 29.7 g (0.1058 mole) of 5-(4-chlorobutyl)-3-phenylmethyleneamino-2-oxazolidinone.

VI. Synthesis of 5-[4-(4-Methyl-1-piperazinyl)butyl]-3-phenylmethyleneamino-2-oxazolidinone A stirred mixture of 5-(4-chlorobutyl)-3-phenylmethylene-amino-2-oxazolidinone (29.7 g, 0.1058 mole), dimethylformamide (600 ml) and 1-methylpiperazine (26.5 g, 0.2645 mole) is heated to reflux. Reflux is maintained 3.5 hours. After cooling to ambient temperature, the solution is concentrated under reduced pressure to a semi-solid residue. This residue is dissolved in $CH_2Cl_2$ (600 ml), washed with saturated $NaHCO_3$ (2×300 ml, 2×200 ml), $H_2O$ (2×100 ml), saturated NaCl (1×200 ml) and dried over $MgSO_4$. The filtered solution is concentrated under reduced pressure to a solid residue. This is triturated in hexane (2×300 ml), decanting the supernatant then evaporating to dryness, giving 31.0 g (0.090 mole) of 5-[4-(4-methyl-1-piperazinyl)butyl]-3-phenylmethyleneamino-2-oxazolidinone.

VII. Synthesis of 3-[[[5-(4-Chlorophenyl)-2-furanyl]methylene]-amino]-5-[4-(4-methyl-1-piperazinyl)butyl]-2-oxazolidinone Dihydrochloride A mixture of 5-[4-(4-methyl-1-piperazinyl)butyl]-3-phenyl methyleneamino-2-oxazolidinone (2.88 g, 0.0087 mole), 2N HCl (125 ml) and 5% Pd/C:50% $H_2O$ (2 g) is subjected to $H_2$ on a Parr apparatus at 40 psi at ambient temperature. After 2 hours, $H_2$ uptake is stopped at 100% of theory. The catalyst is removed by filtration and the filtrate concentrated under reduced pressure to an oily residue. The residue is azeotroped with absolute ethanol (4×20 ml), giving a semi-solid residue.

This residue, dimethylformamide (75 ml) and 5-(4-chlorophenyl)-2-furancarboxaldehyde [prepared as described in U.S. Pat. No. 4/882,354 to Huang et al. (assigned to Norwich Eaton Pharmaceuticals, Inc.,) issued Nov. 21, 1984; see cols. 7 & 8] (1.8 g, 0.0087 mole) are stirred at ambient temperature overnight. After cooling on an ice bath, the solid is collected and air-dried. This is recrystallized from absolute EtOH/$H_2O$, collected, washed with absolute ethanol (20 ml), air-dried, dried at 90° C. and dried in vacuo at 77° C. to give 2.8 g (0.0070 mole) of 3-[[[5-(4-chlorophenyl)-2-furanyl]methylene]amino]-5-[4-(4-methyl-1-piperazinyl)butyl]-2-oxazolidinone dihydrochloride.

EXAMPLE G

Preparation of a 3-[[[5-(4-Chlorophenyl)-2-furanyl]methylene]amino]-5-[3-(4-methyl-1-piperazinly) propyl]-2-oxazolidinone Dihydrochloride Oral Tablet A tablet combining the compound, 3-[[[5-(4-chlorophenyl)-2-furanyl]methylene]amino]-5-[3-(4-methyl- 1-piperazinyl)propyl]-2-oxazolidinone dihydrochloride, [prepared as described in Example E herein] has the following composition.

| ACTIVE INGREDIENT | |
|---|---|
| 3-[[[5-(4-Chlorophenyl)-2-furanyl] methylene]amino]-5-[3-(4-methyl-1-piperazinyl)propyl]-2-oxazolidinone dihydrochloride | 350 mg |
| EXCIPIENTS | |
| Lactose | 197 mg |
| Sodium Starch Glycolate | 50 mg |
| Pregelatinized Starch | 30 mg |
| Talc | 12 mg |
| Magnesium Stearate | 6 mg |

Ten thousand tablets having the above composition are prepared as described below:

3.50 kg of 3-[[[5-(4-Chlorophenyl)-2-furanyl] methylene]-amino]-5-[3-(4-methyl-1-piperazinyl)propyl]-2-oxazolidinone dihydrochloride, 1.92 kg of lactose, 0.50 kg of sodium starch glycolate, and 0.30 kg of pregelatinized starch are blended in a Patterson-Kelly blender and then granulated with water using the intensifier bar.

The granulation is next dried on trays in an oven or in a fluid bed dryer.

The granulation is milled through a 12-mesh screen using an oscillator or other suitable mill.

The granulation is blended with 120 g of talc and 60 g of magnesium stearate.

The talc magnesium and granulation mixture is compressed into 440 mg tablets on a suitable tablet machine.

A patient with cardiac arrhythmia and/or cardiac fibrillation is given the above tablet in a suitable dosage regimen.

EXAMPLE H

Preparation of a 3-[[[5-(4-Chlorophenyl)-2-furanyl] methylene]amino]-5-[3-(1-piperidinyl)propyl]-2-oxazolidinone Hydrochloride Oral Tablet An oral tablet containing 3-[[[5-(4-chlorophenyl)-2-furanyl]methylene]amino]-5-[3-(1-piperidinyl)propyl]-2-oxazolidinone hydrochloride [prepared as described in Example D herein], has the following composition:

| ACTIVE INGREDIENT | |
|---|---|
| 3-[[[5-(4-Chlorophenyl)-2-furanyl]methylene]amino]-5-[3-(1-piperidinyl)propyl]-2-oxazolidinone dihydrochloride | 300 mg |
| EXCIPIENTS | |
| Dibasic Calcium Phosphate | 219 mg |
| Crospovidone | 60 mg |
| Povidone | 12 mg |
| Talc | 6 mg |
| Magnesium Stearate | 3 mg |

Ten thousand tablets having the above composition are prepared as described below:

3.00 kg of 3-[[[5-(4-chlorophenyl)-2-furanyl]methylene]-amino]-5-[3-(1-piperidinyl)propyl]-2-oxazolidinonehydrochloride, 219 kg of dibasic calcium phosphate, 0.60 kg of crospovidone, and 0.12 kg of povidone are blended in a Patterson-Kelly blender and then granulated with water using the intensifier bar.

The granulation is dried on trays in an oven or in a fluid bed dryer. The granulation is next milled through a 12 mesh screen using an oscillator or other suitable mill.

The granulation is blended with 60 g of talc and 30 g of magnesium stearate. Finally, the granulation, talc, and magnesium stearate mixture are compressed into 600 mg tablets on a suitable tablet machine.

A patient suffering from cardiac arrhythmia and/or cardiac fibrillation is given the oral tablet utilizing suitable dosage regimen.

EXAMPLE I

Preparation of a 3-[[[5-(4-Chlorophenyl)-2-furanyl] methylene]amino]-5-[4-(4-methyl-1-piperazinyl) butyl]-2-oxazolidinone Dihydrochloride Oral Capsule An oral capsule containing 3[[[5-(4-chlorophenyl)-2-furanyl]methylene]amino]-5-[4-(4-methyl-1-piperazinyl) butyl]-2-oxazolidinone dihydrochloride [prepared as described in Example F herein] has the following composition:

| ACTIVE INGREDIENT | |
|---|---|
| 3[[[5-(4-Chlorophenyl)-2-furanyl]methylene]amino]-5-[4-(4-methyl-1-piperazinyl)butyl]-2-oxazolidinone dihydrochloride | 300 mg |
| EXCIPIENTS | |
| Lactose | 92 mg |
| Sodium Starch Glycolate | 40 mg |
| Pregelatinized Starch | 25 mg |
| Talc | 12 mg |
| Magnesium Stearate | 3 mg |
| Hard Gelatin Capsule Shell | 1 per capsule |

Ten thousand oral capsules having the above composition are prepared as described below:

3.00 kg of 3[[[5-(4-chlorophenyl)-2-furanyl]methylene]-amino]-5-[4-(4-methyl-1-piperazinyl)butyl]-2-oxazolidinone dihydrochloride, 0.92 kg of lactose, 0.40 kg of sodium starch glycolate, and 0.25 kg of pregelatinized starch are blended in a Patterson-Kelly blender and granulated with water using the intensifier bar.

The granulation is dried on trays in an oven or in a fluid bed dryer.

The granulation is milled through a 12-mesh screen using an oscillator or other suitable mill. The granulation is blended with 120 g of talc and 30 g of magnesium stearate.

Finally, 472 mg of granulation, talc, and magnesium stearate mixture is filled into each capsule shell on a suitable capsule filling machine.

A patient suffering from cardiac arrhythmia and/or cardiac fibrillation is given the oral capsules prepared as described above, utilizing a suitable dosage regimen.

EXAMPLE J

Preparation of a 3-[[[5-(4-Chlorophenyl)-2-furanyl] methylene]amino]-5-[4-(4-methyl-1-piperazinyl) butyl]-2-oxazolidinone Dihydrochloride Oral Tablet An oral capsule containing 3-[[[5-(4-chlorophenyl)-2-furanyl]methylene]amino]-5-[4-(4-methyl-1-piperazinyl) butyl]-2-oxazolidinone dihydrochloride [prepared as described in Example F herein] has the following composition:

| ACTIVE INGREDIENT | |
| --- | --- |
| 3-[[[5-(4-Chlorophenyl)-2-furanyl]methylene]amino]-5-[4-(4-methyl-1-piperazinyl)butyl]-2-oxazolidinone dihydrochloride | 175 mg |
| EXCIPIENTS | |
| Microcrystalline Cellulose | 110 mg |
| Crospovidone | 25 mg |
| Povidone | 5 mg |
| Talc | 5 mg |
| Magnesium Stearate | 2 mg |
| Hard Gelatin Capsule Shell | 1 per capsule |

Ten thousand capsules having the above composition are prepared as described below:

1.75 kg of 3-[[[5-(4-chlorophenyl)-2-furanyl]methylene]amino]-5[4-(4-methyl-1-piperazinyl)butyl]-2-oxazolidinone dihydrochloride, 1.10 kg of microcrystalline cellulose, 0.25 kg of crospovidone, and 0.05 kg of povidone are blended in a Patterson-Kelly or other suitable blender and then granulated with water using the intensifier bar.

The granulation is dried on trays in an oven or a fluid bed dryer. The granulation is milled through a 12 mesh screen using an oscillator or other suitable mill. The granulation is blended with 50 g of talc and 20 g of magnesium stearate.

322 mg of the granulation, talc, and magnesium stearate mixture is filled into each capsule shell on a suitable capsule filling machine.

A patient suffering from cardiac arrhythmia and/or cardiac fibrillation is given the oral capsule prepared as described above in a suitable dosage regimen.

EXAMPLE K

Preparation of a 3-[[[5-(4-Chlorophenyl-2-furanyl]methylene]amino]-5-[3-(4-methyl-1-piperazinyl)propyl]-2-oxazolidinone Dihydrochloride Lyophilized Injection A solution suitable for use as an intravenous (I.V.) injection containing 3-[[[5-(4-chlorophenyl-2-furanyl]methylene]amino]-5-[3-(4-methyl-1-piperazinyl)propyl]-2-oxazolidinone dihydrochloride [prepared as described in Example D herein] has the following composition:

| ACTIVE INGREDIENT | |
| --- | --- |
| 3-[[[5-(4-Chlorophenyl-2-furanyl]methylene]amino]-5-[3-(4-methyl-1-piperazinyl)propyl]-2-oxazolidinone dihydrochloride | 400 mg |
| EXCIPIENTS | |
| Mannitol | 500 mg |
| Citric Acid/Sodium Citrate | -quantity sufficient to adjust pH to 5.5–6.5 |

The procedure to make 1,000 vials of the above solution for I.V. injection is prepared as described hereinbelow.

400 g of 3-[[[5-(4-chlorophenyl-2-furanyl]methylene]amino]-5-[3-(4-methyl-1-piperazinyl)propyl]-2-oxazolidinone dihydrochloride, 500 g mannitol, and sufficient sodium citrate and/or citric acid to make a pH 5.5 to 6.5 solution are dissolved in 10.0 liters of sterile water for injection.

The resulting solution is aseptically filtered through a 0.2 micron filter and filled into vials in the amount of 10 ml per vial.

The vials are loaded into a lyophilizer, frozen, dried and stoppered. The lyophilized product is diluted with 10 ml of sterile water immediately prior to injection. A patient suffering from cardiac arrhythmia and/or cardiac fibrillation is given an I.V. injection of the solution prepared as described above, utilizing a suitable dosage regimen.

EXAMPLE L

Any of the cyclic urethane compounds prepared as described in Examples A–F herein can be utilized as the active ingredient in any of the dosage forms prepared as described in Examples G–K herein.

EXAMPLE M

A 57-year-old Caucasian male is found unconscious and without palpable pulse at home. A family member initiates cardiopulmonary resuscitation. The first rhythm documented by the rescue squad is ventricular fibrillation. The patient is successfully resuscitated.

The patient had had a myocardial infarction three years ago, and has had stable angina since.

During the ensuing hospitalization, the patient is found not to have had a myocardial infarction. Monomorphic sustained ventricular tachyarrhythmia is induced by programmed electrical stimulation.

The patient's cardiologist prescribes 3-[[[5-(4-Chlorophenyl)-2-furanyl]methylene]amino]-5-[3-(4-methyl-1-piperazinyl)propyl]-2-oxazolidinone dihydrochloride at an oral dose of 350 mg, twice a day, after meals. After four days of therapy, the arrhythmia is not inducible at a repeat programmed electrical stimulation study. The patient has no further episodes of cardiac arrest over the next 2 years, and treatment will continue.

EXAMPLE N

A 65-year-old black male has a syncopal spell preceded by sensations of palpitations. Over the preceding several months, the patient had experienced frequent palpitations, once with a near-fainting spell. He has a history of hypertensive cardiovascular disease, diabetes, remote myocardial infarction, and obesity.

Sustained monomorphic ventricular tachycardia is induced by programmed electrical stimulation. The patient's cardiologist prescribes 3-[[[5-(4-chlorophenyl)-2-furanyl]methylene]-amino]-5-(3-(piperidinyl)propyl]-2-oxazolidinone hydrochloride at an oral dose of 300 mg, once a day, after a meal. After several days of therapy, the arrhythmia is noninducible on repeat programmed electrical stimulation. There are no further episodes of syncope or presyncope over the next three years of observation.

EXAMPLE O

A 58-year-old female Oriental patient with a cardiomyopathy presents with recurrent syncope. Her ejection fraction is 35%. Programmed electrical stimulation (PES) induces poorly tolerated sustained ventricular tachyarrhythmia, unresponsive to three different antiarrhythmic drugs. A fourth drug, moricizine, reduces the rate of the tachyarrhythmia and is continued, but the tachyarrhythmia still induces hypotension. She undergoes implantation of an automatic implantable cardioverter-defibrillator (AICD).

The defibrillator discharges twice in the year after implantation of the AICD. The device's monitor records sustained ventricular tachyarrhythmia at the times of defibrillation. After the second discharge, the patient is hospitalized. Sustained monomorphic ventricular tachyarrhythmia is induced at PES. Moricizine is discontinued and 3-[[[5-(4-Chlorophenyl)-2-furanyl]methylene]amino]-5-[3-(4-methyl-1-piperazinyl)propyl]-2-oxazolidinone dihydrochloride at an oral dose of 350 mg, twice a day, after meals, is started by the patient's cardiologist.

At repeat PES several days later, the arrhythmia is not inducible and the defibrillation threshold is unchanged. Over the subsequent year of observation, no further discharges of the AICD are experienced.

EXAMPLE P

A 35-year-old female presents with a 15-year history of frequent (2/month) spells of rapid heartbeat lasting several hours associated with dizziness and fatigue. These spells cause her to miss time from work.

A transtelephonic event monitor demonstrates paroxysmal supraventricular tachycardia. The patient's physician prescribes 3-[[[5-(4-Chlorophenyl)-2-furanyl]methylene]amino]-5-[3-(piperidinyl)propyl]-2-oxazolidinone hydrochloride at an oral dose of 175 mg, once a day, after a meal.

Over the subsequent year of observation, the frequency of these spells decreases to one every other month, with marked improvement in her attendance record at work.

EXAMPLE Q

A 75-year-old Caucasian male who has a fifty pack per year history of smoking has known episodes of atrial fibrillation documented by transtelephonic monitoring, at the rate of three per month while on therapy with digoxin and quinidine. These spells sometimes last over eight hours and prevent the patient's pursuit of his normal daily activities, such as gardening, due to weakness.

The patient's physician switches the patient from quinidine to 3-[[[5-(4-Chlorophenyl)-2-furanyl]methylene]amino]-5-[3-(piperidinyl)propyl]-2-oxazolidinone hydrochloride orally at a dose of 175 mg, once a day, after a meal. The frequency of spells decreases to one a month over the subsequent four months of observation.

EXAMPLE R

A 40-year-old Caucasian male has a several year history of frequent palpitations. The patient experiences anxiety and shortness of breath at the time of the palpitations, and has become preoccupied by a fear of death. Extensive evaluations have demonstrated an absence of structural heart disease. Holter monitoring has shown 2500 PVCs per day, unifocal, with 50 couplets per day. Neither reassurance nor subsequent therapy with propranolol have been effective.

The physician prescribes 3-[[[5-(4-Chlorophenyl)-2-furanyl]-methylene]amino]5-[3-(4-methyl-1-piperazinyl)propyl]-2-oxazolidinone dihydrochloride at an oral dose of 350 mg, once a day, after a meal.

The frequency of the palpitations decreases and the associated anxiety and shortness of breath are relieved. Holter monitoring now shows 250 PVCs per day and no repetitive forms. The preoccupation with death resolves over several months. The patient is monitored closely, and continues to do well over the subsequent five years.

EXAMPLE S

A fifty-eight-year old black male with a ten year history of non-insulin dependent diabetes mellitus and a cholesterol level exceeding 300 mg/dl has a myocardial infarction. Two weeks after the infarction, he is asymptomatic with the exception of dyspnea on exertion. His ejection fraction is 29%, and 24 hour Holter monitoring reveals 50 unifocal PVCs per hour, occasional couplets, and one five beat run of ventricular tachyarrhythmia.

His cardiologist prescribes 3-[[[5-(4-Chlorophenyl)-2-furanyl]methylene]amino]-5-[3-(4-methyl-1-piperazinyl)propyl]-2-oxazolidinone dihydrochloride at an oral dose of 350 mg, once a day, after a meal. Repeat Holter monitoring shows abolition of all repetitive forms and an average of 9 PVCs per hour. The patient does well over the next three years of follow up observation.

What is claimed is:

1. A cyclic urethane compound having the structure:

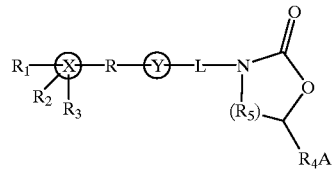

wherein a) X is an unsaturated 6 membered carbocycle;

b) R is a covalent bond;

c) Y is furyl;

d) $R_1$, $R_2$, and $R_3$ are independently selected from the group consisting of H, Cl, $NO_2$, F, Br, $NH_2$, $CF_3$, OH, $SO_3H$, $CH_3SO_2NH$, COOH, unsubstituted $C_1$–$C_4$ alkoxy, unsubstituted $C_1$–$C_4$ alkoxycarbonyl, unsubstituted $C_1$–$C_4$ alkyl, hydroxy-unsubstituted $C_1$–$C_4$ alkyl, carboxy-unsubstituted $C_1$–$C_4$ alkyl, amino-unsubstituted $C_1$–$C_4$ alkyl, unsubstituted $C_2$–$C_5$ acyloxy, and unsubstituted $C_2$–$C_5$ acylamino;

e) L is unsubstituted $C_1$–$C_4$ alkylimino; wherein the carbon-containing end of L is bound to Y; and wherein the nitrogen atom of L is bound to the nitrogen atom at the 3-position of the cyclic urethane ring moiety;

f) $R_4$ is unsubstituted $C_1$–$C_4$ alkylene;

g) A is a 6-membered saturated heterocycle selected from the group consisting of piperidino and piperazino wherein N is covalently bound to $R_4$; and h) $R_5$ is methylene;

and the pharmaceutically-acceptable salts and esters thereof.

2. A compound according to claim 1 wherein $R_1$, $R_2$, and $R_3$ are independently selected from the group consisting of H, Cl, F, Br, $CH_3$ and OH.

3. The compound of claim 1, wherein A is selected from:

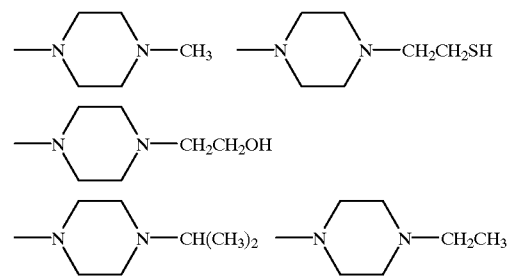

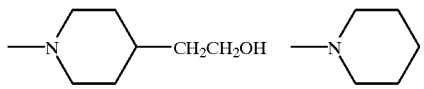

and the pharmaceutically-acceptable salts and esters thereof.

4. The compound of claim 1, wherein X is 2-acetoxy-5-chlorophenyl; 3-hydroxy-5-hydroxymethyl-2-methylphenyl; 5-methoxycarbonylphenyl; 5-chloro-2-hydroxyphenyl; 5-chloro-2-methoxyphenyl; 2-methanesulfonylaminophenyl; 3-aminophenyl; 2-methoxyphenyl; 3-methoxyphenyl; 2-aminophenyl; 3,5-dimethyl-4-hydroxyphenyl; 4-carboxyphenyl.

5. A compound according to claim 2 of formula

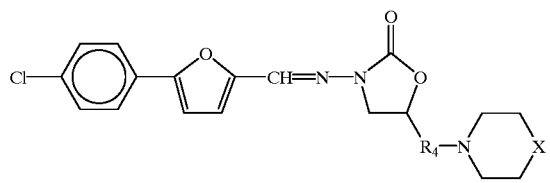

wherein
a) $R_4$ is a $C_1$ to $C_4$ unsubstituted alkyl;
b) X is $CH_2$, $NCH_3$ or $NCH_2CH_2OH$.

6. A compound according to claim 2 of formula

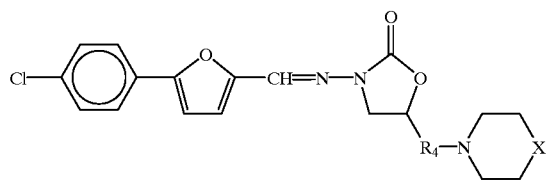

wherein
a) $R_4$ is of formula $(CH_2)_n$ and n is from 1 to 4;
b) X is $CH_2$, $NCH_3$, or $NCH_2CH_2OH$.

7. A compound according to claim 1, selected from the group consisting of:
  3-[[[5-(4-chlorophenyl)-2-furanyl]methylene]amino]-5-(1-piperidinylmethyl)-2-oxazolidinone;
  3-[[[5-(4-chlorophenyl)-2-furanyl]methylene]amino]-5-[3-(1-piperidinyl)propyl]-2-oxazolidinone;
  3-[[[5-(4-chlorophenyl)-2-furanyl]methylene]amino]-5-[4-(4-methyl-1-piperazinyl))butyl]-2-oxazolidinone;
  3-[[[5-(4-chlorophenyl)-2-furanyl]methylene]amino]-5-[3-(4-methyl-1-piperazinyl)propyl ]-2-oxazolidinone;
  3-[[[5-(4-chlorophenyl)-2-furanyl]methylene]amino]-5-[[4-(2-hydroxyethyl)-1-piperidinyl ]-methyl]-2-oxazolidinone;
  3-[[[5-(4-chlorophenyl)-2-furanyl]methylene]amino]-5-[(4-methyl-1-piperazinyl)methyl]-2-oxazolidinone;
  and the pharmaceutically-acceptable salts thereof.

8. A compound according to claim 7, wherein the salt is a hydrochloride salt.

9. A compound according to claim 7, wherein the compound 3-[[[5-(4-chlorophenyl)-2-furanyl]methylene] amino]-5-[3-(1-piperidinyl)propyl]-2-oxazolidinone or its hydrochloride salt.

10. Either enantiomer of the compound according to claim 9.

11. A pharmaceutical composition for the treatment of cardiac arrhythmia or cardiac fibrillation comprising an effective amount of a compound of claim 1, or any mixtures thereof, and one or more pharmaceutically-acceptable excipients.

12. A pharmaceutical composition for the treatment of cardiac arrhythmia or cardiac fibrillation comprised of from 15 to 90% of a cyclic urethane compound of claim 1, or any mixtures thereof, and from 10 to 85% pharmaceutically-acceptable excipients.

13. A pharmaceutical composition according to claim 11, wherein the pharmaceutically-acceptable excipients are selected from the group consisting of polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

14. A pharmaceutical composition according to claim 12 comprised of from 15–90% of a cyclic urethane active ingredient, or mixture thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

15. A method of treatment for cardiac arrhythmias and/or cardiac fibrillation comprised of administering an effective amount of a compound according to claim 1.

16. A method of treatment for cardiac arrhythmias and/or cardiac fibrillation comprised of administering an effective amount of a compound according to claim 1, wherein the compound is selected from the group consisting of:
  3-[[[5-(4-chlorophenyl)-2-furanyl]methylene]amino]-5-(1 -piperidinylmethyl)-2-oxazolidinone;
  3-[[[5-(4-chlorophenyl)-2-furanyl]methylene]amino]-5-[3-(1-piperidinyl)propyl]-2-oxazolidinone;
  3-[[[5-(4-chlorophenyl)-2-furanyl]methylene]amino]-5-[4-(4-methyl-1-piperazinyl))butyl]-2-oxazolidinone;
  3-[[[5-(4-chlorophenyl)-2-furanyl]methylene]amino]-5-[3-(4-methyl-1-piperazinyl)propyl]-2-oxazolidinone;
  3-[[[5-(4-chlorophenyl)-2-furany]methylene]amino]-5-[[4-(2-hydroxyethyl)-1-piperidinyl ]-methyl]-2-oxazolidinone.
  3-[[[5-(4-chlorophenyl)-2-furanyl]methylene]amino]-5-[(4-methyl-1-piperazinyl)methyl]-2-oxazolidinone;
and the pharmaceutically-acceptable hydrochloride salts thereof.

* * * * *